United States Patent
Wu

(10) Patent No.: US 10,646,445 B2
(45) Date of Patent: *May 12, 2020

(54) ANALYSIS COMPENSATION INCLUDING SEGMENTED SIGNALS CONVERTED INTO SIGNAL PROCESSING PARAMETERS FOR DESCRIBING A PORTION OF TOTAL ERROR

(71) Applicant: Ascensia Diabetes Care Holdings AG, Basel (CH)

(72) Inventor: Huan-Ping Wu, Granger, IN (US)

(73) Assignee: Ascensia Diabetes Care Holdings AG, Basel (CH)

(*) Notice: Subject to any disclaimer, the term of this patent is extended or adjusted under 35 U.S.C. 154(b) by 340 days.

This patent is subject to a terminal disclaimer.

(21) Appl. No.: 15/690,014

(22) Filed: Aug. 29, 2017

(65) Prior Publication Data

US 2017/0360712 A1    Dec. 21, 2017

Related U.S. Application Data

(63) Continuation of application No. 13/623,654, filed on Sep. 20, 2012, now Pat. No. 9,775,806.

(60) Provisional application No. 61/537,145, filed on Sep. 21, 2011.

(51) Int. Cl.
| | | |
|---|---|---|
| *A61K 9/19* | (2006.01) | |
| *A61K 9/00* | (2006.01) | |
| *A61K 47/26* | (2006.01) | |
| *A61K 31/198* | (2006.01) | |
| *G01N 27/327* | (2006.01) | |

(52) U.S. Cl.
CPC .............. *A61K 9/19* (2013.01); *A61K 9/0019* (2013.01); *A61K 31/198* (2013.01); *A61K 47/26* (2013.01); *G01N 27/3274* (2013.01)

(58) Field of Classification Search
None
See application file for complete search history.

(56) References Cited

U.S. PATENT DOCUMENTS

| | | | |
|---|---|---|---|
| 4,431,004 A | 2/1984 | Bessman | |
| 4,750,496 A | 6/1988 | Reinhart | |
| 5,243,516 A | 9/1993 | White | |
| 5,352,351 A | 10/1994 | White et al. | |
| 5,366,609 A | 11/1994 | White et al. | |
| 5,395,504 A | 3/1995 | Saurer et al. | |
| 5,508,171 A | 4/1996 | Walling et al. | |
| 5,582,697 A | 12/1996 | Ikeda et al. | |
| 5,620,579 A | 4/1997 | Genshaw et al. | |
| 5,653,863 A | 8/1997 | Genshaw et al. | |
| 5,723,284 A | 3/1998 | Ye | |
| 5,798,031 A | 8/1998 | Charlton et al. | |
| 6,120,676 A | 9/2000 | Heller et al. | |
| 6,153,069 A | 11/2000 | Pottgen et al. | |
| 6,233,471 B1 | 5/2001 | Berner et al. | |
| 6,275,717 B1 | 8/2001 | Gross et al. | |
| 6,391,645 B1 | 5/2002 | Huang et al. | |
| 6,413,411 B1 | 7/2002 | Pottgen et al. | |
| 6,448,067 B1 | 9/2002 | Tajnafoi | |
| 6,475,372 B1 | 11/2002 | Ohara et al. | |
| 6,531,040 B2 | 3/2003 | Musho et al. | |
| 6,576,117 B1 | 6/2003 | Iketaki et al. | |
| 6,645,368 B1 | 11/2003 | Beaty et al. | |
| 6,797,150 B2 | 9/2004 | Kermani et al. | |
| 6,824,670 B2 | 11/2004 | Tokunaga et al. | |
| 7,118,668 B1 | 10/2006 | Edelbrock et al. | |
| 7,122,110 B2 | 10/2006 | Deng et al. | |
| 7,122,111 B2 | 10/2006 | Tokunaga et al. | |
| 7,132,041 B2 | 11/2006 | Deng et al. | |
| 7,195,704 B2 | 3/2007 | Kermani et al. | |
| 7,338,639 B2 | 3/2008 | Burke et al. | |
| 7,351,323 B2 | 4/2008 | Iketaki et al. | |
| 7,488,601 B2 | 2/2009 | Burke et al. | |

(Continued)

FOREIGN PATENT DOCUMENTS

| | | |
|---|---|---|
| EP | 1742045 | 1/2007 |
| EP | 2040065 A1 | 3/2009 |

(Continued)

OTHER PUBLICATIONS

European Patent Office, International. Search Report and Written Opinion of International Searching Authority for PCT/US2006/028013, dated Dec. 6, 2006 (16 pages).
European Patent Office, International Search Report and Written Opinion of International Searching Authority for PCT/US2007/068320, dated Oct. 19, 2007 (14 pages).
European Patent Office, International Search Report and Written Opinion of International Searching Authority for PCT/US2008/085768, dated Sep. 29, 2009 (16 pages).
European Patent Office, International Search Report and Written Opinion of International Searching Authority for PCT/US2011/029318, dated Jun. 20, 2011 (11 pages).
European Patent Office, International Search Report and Written Opinion of International Searching Authority for PCT/US2012/056280, dated Feb. 25, 2013 (17 pages).

(Continued)

Primary Examiner — G Steven Vanni
(74) Attorney, Agent, or Firm — Nixon Peabody LLP

(57) ABSTRACT

A biosensor system determines analyte concentration from an output signal generated from a light-identifiable species or a redox reaction of the analyte. The biosensor system compensates at least 50% of the total error in the output signal with a primary function and may compensate a portion of the residual error with at least one residual function. An SSP function may serve as the primary function, first residual function, or second residual function. Preferably, when the SSP function serves as the first residual function, the SSP function compensates at least 50% of the residual error remaining after primary compensation. Preferably, when the SSP function serves as the second residual function, the SSP function compensates at least 50% of the residual error remaining after primary and first residual compensation. The error compensation provided by the primary, first residual, and second residual functions may be adjusted with function weighing coefficients.

21 Claims, 21 Drawing Sheets

(56) References Cited

U.S. PATENT DOCUMENTS

| | | | |
|---|---|---|---|
| 7,491,310 | B2 | 2/2009 | Okuda et al. |
| 7,501,052 | B2 | 3/2009 | Iyenga et al. |
| 7,517,439 | B2 | 4/2009 | Harding et al. |
| 7,966,859 | B2 | 6/2011 | Wu et al. |
| 8,002,965 | B2 | 8/2011 | Beer et al. |
| 8,068,272 | B2 | 11/2011 | LeCain et al. |
| 8,101,062 | B2 | 1/2012 | Deng |
| 8,287,704 | B2 | 10/2012 | Shinno |
| 2002/0084196 | A1 | 7/2002 | Liamos et al. |
| 2002/0146835 | A1 | 10/2002 | Modzelewski et al. |
| 2002/0160517 | A1 | 10/2002 | Modzelewski et al. |
| 2004/0072158 | A1 | 4/2004 | Henkens et al. |
| 2004/0079652 | A1 | 4/2004 | Vreke et al. |
| 2004/0256248 | A1 | 12/2004 | Burke et al. |
| 2004/0260511 | A1 | 12/2004 | Burke et al. |
| 2005/0023154 | A1 | 2/2005 | Kermani et al. |
| 2005/0176153 | A1 | 8/2005 | O'hara et al. |
| 2007/0045127 | A1 | 3/2007 | Huang et al. |
| 2007/0231914 | A1 | 10/2007 | Deng et al. |
| 2008/0173552 | A1 | 7/2008 | Wu et al. |
| 2008/0179197 | A1 | 7/2008 | Wu |
| 2008/0248581 | A1 | 10/2008 | Chu et al. |
| 2009/0099787 | A1 | 4/2009 | Carpenter et al. |
| 2009/0177406 | A1 | 7/2009 | Wu |
| 2009/0236237 | A1 | 9/2009 | Shinno et al. |
| 2011/0297554 | A1 | 12/2011 | Wu et al. |
| 2011/0301857 | A1 | 12/2011 | Huang et al. |

FOREIGN PATENT DOCUMENTS

| | | |
|---|---|---|
| JP | 2005147990 | 6/2005 |
| JP | 2009-528540 A | 8/2009 |
| JP | 2010-534838 A | 11/2010 |
| JP | 2011-506966 A | 3/2011 |
| TW | 200933147 A | 8/2009 |
| WO | 1998058250 | 12/1998 |
| WO | 2001021827 | 3/2001 |
| WO | 2003091717 | 4/2003 |
| WO | 2005073393 | 8/2005 |
| WO | 2005078437 | 8/2005 |
| WO | 2006069797 | 8/2006 |
| WO | 2007040913 | 4/2007 |
| WO | 2009108239 | 9/2009 |
| WO | 2008004565 A1 | 12/2009 |
| WO | 2010077660 | 7/2010 |
| WO | 2011059670 | 5/2011 |

OTHER PUBLICATIONS

Gunasingham, et al.; "Pulsed amperometric detection of glucose using a mediated enzyme electrode"; Journal of Electroanalytical Chemistry, vol. 287, No. 2, pp. 349-362; 1990.

Lin et al.; "Reduction of the Interferences of Biochemicals and Hematrocrit Ration on the Determination of Whole Blood Glucose Using Multiple Screen-Printed Carbon Electrode Test Strips"; Anal. Bioanal. Chem., vol. 289, pp. 1623-1631; 2007.

Panteleon, et al.; "The Role of the Independent Variable to Glucose Sensor Calibration"; Diabetes Technology & Therapeutics, vol. 5, No. 3; pp. 401-441; 2003.

Agamatrix, Inc.; "Wavesense. How It Works."; May 30, 2008; retrieved from http://www.wavesense.info/how-it-works (2 pages).

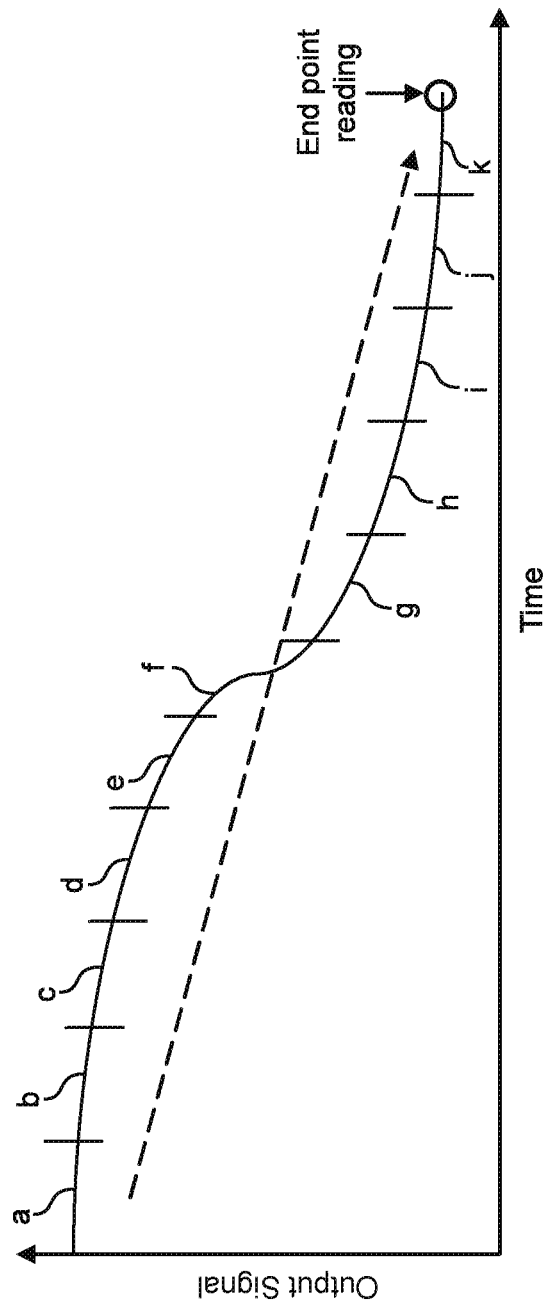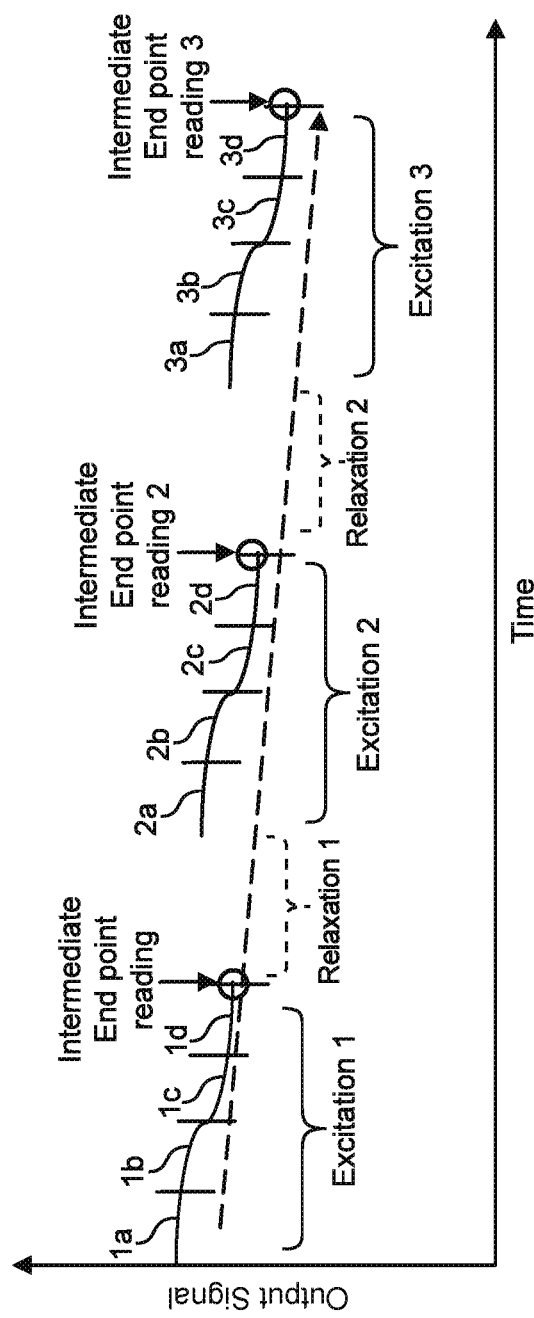
FIG. 1B-1
FIG. 1B-2

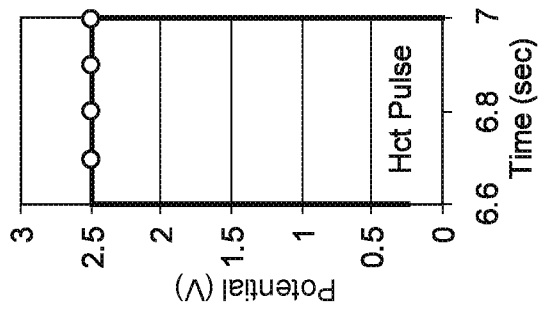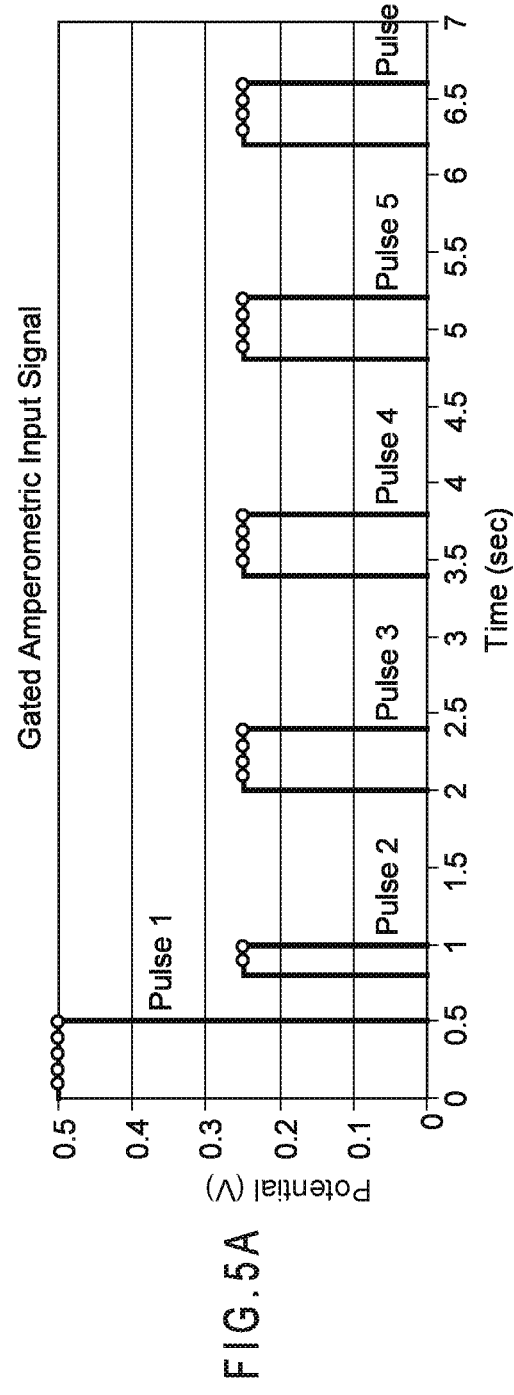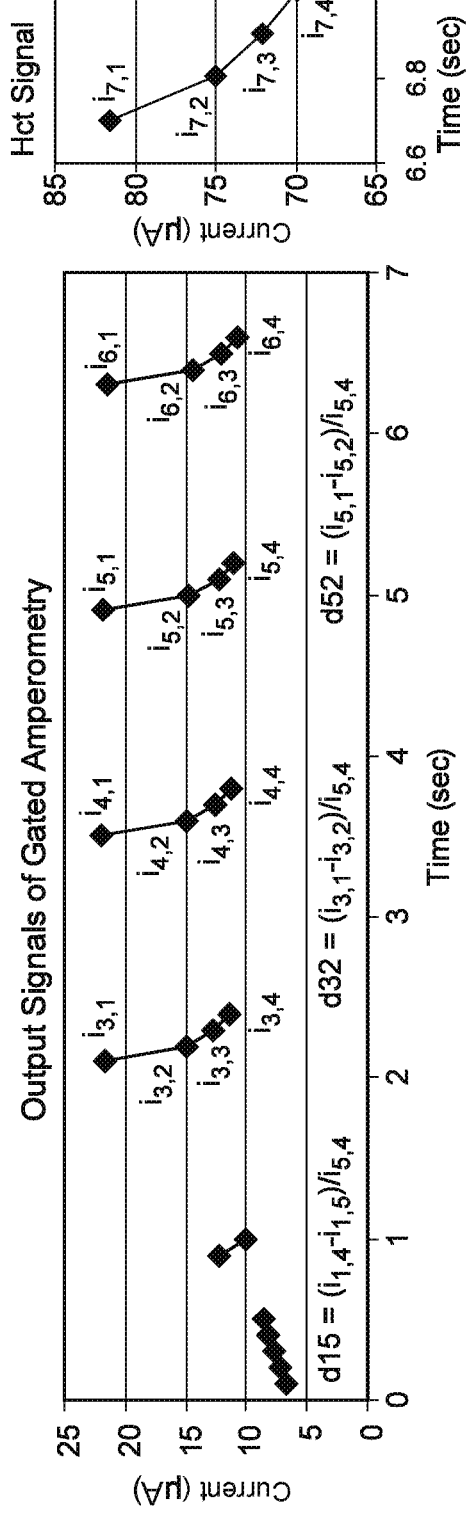
FIG. 5A
FIG. 5B

ANALYSIS COMPENSATION INCLUDING SEGMENTED SIGNALS CONVERTED INTO SIGNAL PROCESSING PARAMETERS FOR DESCRIBING A PORTION OF TOTAL ERROR

REFERENCE TO RELATED APPLICATIONS

This application is a continuation of U.S. application Ser. No. 13/623,654, filed Sep. 20, 2012, and titled "Analysis Compensation Including Segmented Signals," now allowed, which claims the benefit of U.S. Provisional Application No. 61/537,145, filed Sep. 21, 2011, and titled "Analysis Compensation Including Segmented Signal Processing", each of which is hereby incorporated by reference in its entirety.

BACKGROUND

Biosensor systems provide an analysis of a biological fluid sample, such as blood, serum, plasma, urine, saliva, interstitial, or intracellular fluid. Typically, the systems include a measurement device that analyzes a sample residing in a test sensor. The sample usually is in liquid form and in addition to being a biological fluid, may be the derivative of a biological fluid, such as an extract, a dilution, a filtrate, or a reconstituted precipitate. The analysis performed by the biosensor system determines the presence and/or concentration of one or more analytes, such as alcohol, glucose, uric acid, lactate, cholesterol, bilirubin, free fatty acids, triglycerides, proteins, ketones, phenylalanine or enzymes, in the biological fluid. The analysis may be useful in the diagnosis and treatment of physiological abnormalities. For example, a person with diabetes may use a biosensor system to determine the glucose level in blood for adjustments to diet and/or medication.

In blood samples including hemoglobin (Hb), the presence and/or concentration of total hemoglobin and glycated hemoglobin (HbA1c) may be determined. HbA1c (%-A1c) is a reflection of the state of glucose control in diabetic patients, providing insight into the average glucose control over the three months preceding the test. For diabetic individuals, an accurate measurement of %-A1c assists in the determination of the blood glucose level, as adjustments to diet and/or medication are based on these levels.

Biosensor systems may be designed to analyze one or more analytes and may use different volumes of biological fluids. Some systems may analyze a single drop of blood, such as from 0.25-15 microliters (μL) in volume. Biosensor systems may be implemented using bench-top, portable, and like measurement devices. Portable measurement devices may be hand-held and allow for the identification and/or quantification of one or more analytes in a sample. Examples of portable measurement systems include the Elite® meters of Bayer HealthCare in Tarrytown, N.Y., while examples of bench-top measurement systems include the Electrochemical Workstation available from CH Instruments in Austin, Tex.

Biosensor systems may use optical and/or electrochemical methods to analyze the biological fluid. In some optical systems, the analyte concentration is determined by measuring light that has interacted with or been absorbed by a light-identifiable species, such as the analyte or a reaction or product formed from a chemical indicator reacting with the analyte. In other optical systems, a chemical indicator fluoresces or emits light in response to the analyte when illuminated by an excitation beam. The light may be converted into an electrical output signal, such as current or potential, which may be similarly processed to the output signal from an electrochemical system. In either optical system, the system measures and correlates the light with the analyte concentration of the sample.

In light-absorption optical systems, the chemical indicator produces a reaction product that absorbs light. A chemical indicator such as tetrazolium along with an enzyme such as diaphorase may be used. Tetrazolium usually forms formazan (a chromagen) in response to the redox reaction of the analyte. An incident input beam from a light source is directed toward the sample. The light source may be a laser, a light emitting diode, or the like. The incident beam may have a wavelength selected for absorption by the reaction product. As the incident beam passes through the sample, the reaction product absorbs a portion of the incident beam, thus attenuating or reducing the intensity of the incident beam. The incident beam may be reflected back from or transmitted through the sample to a detector. The detector collects and measures the attenuated incident beam (output signal). The amount of light attenuated by the reaction product is an indication of the analyte concentration in the sample.

In light-generated optical systems, the chemical detector fluoresces or emits light in response to the analyte redox reaction. A detector collects and measures the generated light (output signal). The amount of light produced by the chemical indicator is an indication of the analyte concentration in the sample.

An example of an optical system using reflectance is a laminar flow A1c system that determines the concentration of A1c hemoglobin in blood. These systems use immunoassay chemistry where the blood is introduced to the test sensor where it reacts with reagents and then flows along a reagent membrane. When contacted by the blood, A1c antibody coated color beads release and move along with the blood sample to a detection zone 1. Because of the competition between the A1c in the blood sample and an A1c peptide present in detection zone 1 for the color beads, color beads not attached to the A1c antibody are captured at zone 1 and are thus detected as the A1c signal from the change in reflectance. The total hemoglobin (THb) in the blood sample also is reacting with other blood treatment reagents and moves downstream into detection zone 2, where it is measured at a different wavelength. For determining the concentration of A1c in the blood sample, the reflectance signal is proportional to the A1c analyte concentration (%-A1c). For the THb measurement, however, the reflectance in zone 2 is inversely proportional to the THb (mg/dL) for the detection system.

In electrochemical systems, the analyte concentration is determined from an electrical signal generated by an oxidation/reduction or redox reaction of the analyte or a species responsive to the analyte when an input signal is applied to the sample. The input signal may be a potential or current and may be constant, variable, or a combination thereof such as when an AC signal is applied with a DC signal offset. The input signal may be applied as a single pulse or in multiple pulses, sequences, or cycles. An enzyme or similar species may be added to the sample to enhance the electron transfer from a first species to a second species during the redox reaction. The enzyme or similar species may react with a single analyte, thus providing specificity to a portion of the generated output signal. A mediator may be used to maintain the oxidation state of the enzyme and/or assist with electron transfer from the analyte to an electrode.

Electrochemical biosensor systems usually include a measurement device having electrical contacts that connect with the electrical conductors of the test sensor. The conductors may be made from conductive materials, such as solid metals, metal pastes, conductive carbon, conductive carbon pastes, conductive polymers, and the like. The electrical conductors typically connect to working, counter, reference, and/or other electrodes that extend into a sample reservoir. One or more electrical conductors also may extend into the sample reservoir to provide functionality not provided by the electrodes.

The measurement device applies an input signal through the electrical contacts to the electrical conductors of the test sensor. The electrical conductors convey the input signal through the electrodes into the sample present in the sample reservoir. The redox reaction of the analyte generates an electrical output signal in response to the input signal. The electrical output signal from the test sensor may be a current (as generated by amperometry or voltammetry), a potential (as generated by potentiometry/galvanometry), or an accumulated charge (as generated by coulometry). The measurement device may have the processing capability to measure and correlate the output signal with the presence and/or concentration of one or more analytes in the sample.

In coulometry, a potential is applied to the sample to exhaustively oxidize or reduce the analyte. A biosensor system using coulometry is described in U.S. Pat. No. 6,120,676. In amperometry, an electrical signal of constant potential (voltage) is applied to the electrical conductors of the test sensor while the measured output signal is a current. Biosensor systems using amperometry are described in U.S. Pat. Nos. 5,620,579; 5,653,863; 6,153,069; and 6,413,411. In voltammetry, an electric signal of varying potential is applied to a sample of biological fluid, while the measured output is current. In gated amperometry and gated voltammetry, pulsed inputs are used as described in WO 2007/013915 and WO 2007/040913, respectively.

Output signal values that are responsive to the analyte concentration of the sample include those obtained from the analytic input signal. Output signal values that are substantially independent of values responsive to the analyte concentration of the sample include values responsive to temperature and values substantially responsive to interferents, such as the hematocrit or acetaminophen content of a blood sample when the analyte is glucose, for example. Output signals substantially not responsive to analyte concentration may be referred to as secondary output signals, as they are not primary output signals responsive to the alteration of light by the analyte or analyte responsive indicator, electrochemical redox reaction of the analyte, or analyte responsive redox mediator. Secondary output signals may arise from the sample or from other sources, such as a thermocouple.

In many biosensor systems, the test sensor may be adapted for use outside, inside, or partially inside a living organism. When used outside a living organism, a sample of the biological fluid may be introduced into a sample reservoir in the test sensor. The test sensor may be placed in the measurement device before, after, or during the introduction of the sample for analysis. When inside or partially inside a living organism, the test sensor may be continually immersed in the sample or the sample may be intermittently introduced to the test sensor. The test sensor may include a reservoir that partially isolates a volume of the sample or be open to the sample. When open, the test sensor may take the form of a fiber or other structure placed in contact with the biological fluid. Similarly, the sample may continuously flow through the test sensor, such as for continuous monitoring, or be interrupted, such as for intermittent monitoring, for analysis.

The measurement performance of a biosensor system is defined in terms of accuracy and precision. Accuracy reflects the combined effects of random and systematic error components. Systematic error, or trueness, is the difference between the average value determined from the biosensor system and one or more accepted reference values for the analyte concentration of the biological fluid. Trueness may be expressed in terms of mean bias, with larger mean bias values representing lower trueness and thereby contributing to less accuracy. Precision is the closeness of agreement among multiple analyte readings in relation to a mean. One or more error in the analysis contribute to the bias and/or imprecision of the analyte concentration determined by the biosensor system. A reduction in the analysis error of a biosensor system therefore leads to an increase in accuracy and thus an improvement in measurement performance.

Bias may be expressed in terms of "absolute bias" or "percent bias". Absolute bias is the difference between the determined concentration and the reference concentration, and may be expressed in the units of the measurement, such as mg/dL, while percent bias may be expressed as a percentage of the absolute bias value over 100 mg/dL or the reference analyte concentration of the sample. For glucose concentrations less than 100 mg/dL, percent bias is defined as (the absolute bias over 100 mg/dL)*100. For glucose concentrations of 100 mg/dL and higher, percent bias is defined as the absolute bias over the reference analyte concentration*100. Accepted reference values for the analyte glucose in blood samples may be obtained with a reference instrument, such as the YSI 2300 STAT PLUS™ available from YSI Inc., Yellow Springs, Ohio. Other reference instruments and ways to determine percent bias may be used for other analytes. For the %-A1c measurements, the error may be expressed as either absolute bias or percent bias against the %-A1c reference value for the therapeutic range of 4-12%. Accepted reference values for the %-A1c in blood samples may be obtained with a reference instrument, such as the Tosoh G7 instrument available from Tosoh Corp, Japan.

Hematocrit bias refers to the average difference (systematic error) between the reference glucose concentration obtained with a reference instrument and experimental glucose readings obtained from a biosensor system for samples containing differing hematocrit levels. The difference between the reference and values obtained from the system results from the varying hematocrit level between specific blood samples and may be generally expressed as a percentage by the following equation: % Hct-Bias=$100\% \times (G_m - G_{ref})/G_{ref}$, where $G_m$ is the determined glucose concentration at a specific hematocrit level and $G_{ref}$ is the reference glucose concentration at a reference hematocrit level. The larger the absolute value of the % Hct-bias, the more the hematocrit level of the sample (expressed as % Hct, the percentage of red blood cell volume/sample volume) is reducing the accuracy of the determined glucose concentration.

For example, if blood samples containing identical glucose concentrations, but having hematocrit levels of 20, 40, and 60%, are analyzed, three different glucose concentrations will be reported by a system based on one set of calibration constants (slope and intercept of the 40% hematocrit containing blood sample, for instance). Thus, even though the blood glucose concentrations are the same, the system will report that the 20% hematocrit sample contains more glucose than the 40% hematocrit sample, and that the 60% hematocrit sample contains less glucose than the 40% hematocrit sample. "Hematocrit sensitivity" is an expression of the degree to which changes in the hematocrit level of a sample affect the bias values for an analysis. Hematocrit sensitivity may be defined as the numerical values of the percent biases per percent hematocrit, thus bias/%-bias per % Hct.

Biosensor systems may provide an output signal during the analysis of the biological fluid including error from multiple error sources. These error sources contribute to the total error, which may be reflected in an abnormal output signal, such as when one or more portions or the entire output signal is non-responsive or improperly responsive to the analyte concentration of the sample.

The total error in the output signal may originate from one or more error contributors, such as the physical characteristics of the sample, the environmental aspects of the sample, the operating conditions of the system, the manufacturing variation between test sensor lots, and the like. Physical characteristics of the sample include hematocrit (red blood cell) concentration, interfering substances, such as lipids and proteins, and the like. Interfering substances include ascorbic acid, uric acid, acetaminophen, and the like. Environmental aspects of the sample include temperature, oxygen content of the air, and the like. Operating conditions of the system include underfill conditions when the sample size is not large enough, slow-filling of the sample, intermittent electrical contact between the sample and one or more electrodes in the test sensor, prior degradation of the reagents that interact with the analyte, and the like. Manufacturing variations between test sensor lots include changes in the amount and/or activity of the reagents, changes in the electrode area and/or spacing, changes in the electrical conductivity of the conductors and electrodes, and the like. A test sensor lot is preferably made in a single manufacturing run where lot-to-lot manufacturing variation is substantially reduced or eliminated. Manufacturing variations also may be introduced as the activity of the reagents changes or degrades between the time the test sensor is manufactured and when it is used for an analysis. There may be other contributors or a combination of error contributors that cause error in the analysis.

Percent bias, percent bias standard deviation, mean percent bias, relative error, and hematocrit sensitivity are independent ways to express the measurement performance of a biosensor system. Additional ways may be used to express the measurement performance of a biosensor system.

Percent bias is a representation of the accuracy of the biosensor system in relation to a reference analyte concentration, while the percent bias standard deviation reflects the accuracy of multiple analyses, with regard to error arising from the physical characteristics of the sample, the environmental aspects of the sample, and the operating conditions of the system. Thus, a decrease in percent bias standard deviation represents an increase in the measurement performance of the biosensor system across multiple analyses.

The mean may be determined for the percent biases determined from multiple analyses using test sensors from a single lot to provide a "mean percent bias" for the multiple analyses. The mean percent bias may be determined for a single lot of test sensors by using a subset of the lot, such as 100-140 test sensors, to analyze multiple blood samples.

Relative error is a general expression of error that may be expressed as $\Delta G/G_{ref}$ (relative error)=$(G_{calculated}-G_{ref})/G_{ref}=G_{calculated}/G_{ref}-1$; where $\Delta G$ is the error present in the analysis determined analyte concentration in relation to the reference analyte concentration; $G_{calculated}$ is the analyte concentration determined from the sample during the analysis; and $G_{ref}$ is the analyte concentration of the sample as determined by a reference instrument.

Increasing the measurement performance of the biosensor system by reducing error from these or other sources means that more of the analyte concentrations determined by the biosensor system may be used for accurate therapy by the patient when blood glucose is being monitored, for example. Additionally, the need to discard test sensors and repeat the analysis by the patient also may be reduced.

A test case is a collection of multiple analyses (data population) arising under substantially the same testing conditions using test sensors from the same lot. For example, determined analyte concentration values have typically exhibited poorer measurement performance for user self-testing than for health care professional ("HCP") testing and poorer measurement performance for HCP-testing than for controlled environment testing. This difference in measurement performance may be reflected in larger percent bias standard deviations for analyte concentrations determined through user self-testing than for analyte concentrations determined through HCP-testing or through controlled environment testing. A controlled environment is an environment where physical characteristics and environmental aspects of the sample may be controlled, preferably a laboratory setting. Thus, in a controlled environment, hematocrit concentrations can be fixed and actual sample temperatures can be known and compensated. In a HCP test case, the operating condition error may be reduced or eliminated. In a user self-testing test case, such as a clinical trial, the determined analyte concentrations likely will include error from all types of error sources.

Biosensor systems may have a single source of uncompensated output values responsive to a redox or light-based reaction of the analyte, such as the counter and working electrodes of an electrochemical system. Biosensor systems also may have the optional ability to determine or estimate temperature, such as with one or more thermocouples or other means. In addition to these systems, biosensor systems also may have the ability to generate additional output values external to those from the analyte or from a mediator responsive to the analyte. For example, in an electrochemical test sensor, one or more electrical conductors also may extend into the sample reservoir to provide functionality not provided by the working and counter electrodes. Such conductors may lack one or more of the working electrode reagents, such as the mediator, thus allowing for the subtraction of a background interferent signal from the working electrode signal.

Many biosensor systems include one or more methods to compensate for error associated with an analysis, thus attempting to improve the measurement performance of the biosensor system. Compensation methods may increase the measurement performance of a biosensor system by providing the biosensor system with the ability to compensate for inaccurate analyses, thus increasing the accuracy and/or precision of the concentration values obtained from the system. However, these methods have had difficulty compensating the analyte value obtained from substantially continuous output signals terminating in an end-point reading, which is correlated with the analyte concentration of the sample.

For many continuous processes, such as a Cottrell decay recorded from a relatively long duration potential input signal, the decay characteristics of the output signal may be described from existing theory with a decay constant. However, this constant may be less sensitive or insensitive to the physical characteristics of the sample or the operation conditions of the system.

One method of implementing error compensation is to use a gated input signal as opposed to substantially continuous input signal. In these gated or pulsed systems, the changes in the input signal perturbate the reaction of the sample so that compensation information may be obtained. However, for analysis systems using substantially continuous input signals to drive the reaction (commonly electrochemical coulometry or Cottrell-decay amperometry) and for analysis systems that observe a reaction that is started and observed until an end-point is reached (commonly optical), the compensation information as obtained from a perturbation of the reaction of the sample is unavailable. Even in a sample perturbated by a gated input signal, additional compensation information may be available during the continuous portions of the input signal, which may not otherwise be used by conventional error compensation techniques.

Accordingly, there is an ongoing need for improved biosensor systems, especially those that may provide increasingly accurate determination of sample analyte concentrations when an end-point reading from a substantially continuous output signal is correlated with the analyte concentration of the sample and/or when compensation information is unavailable from a perturbation of the reaction. The systems, devices, and methods of the present invention overcome at least one of the disadvantages associated with conventional biosensor systems.

SUMMARY

In one aspect, the invention provides a method for determining an analyte concentration in a sample that includes applying an input signal to a sample including an analyte; generating an output signal responsive to a concentration of the analyte in the sample and an input signal; determining a compensated value from the output signal in response to a conversion function and a segmented signal processing function; and determining the analyte concentration in the sample with the compensated value. A conversion function may be used to convert the output signal to an uncompensated value prior to compensating the value. The uncompensated value may be an uncompensated analyte concentration value.

In another aspect of the invention, there is a method of determining an analyte concentration in a sample that includes generating an output signal responsive to a concentration of an analyte in a sample and an input signal, determining a compensated value from the output signal in response to a conversion function, a primary function, and a segmented signal processing function, and determining the analyte concentration in the sample from the compensated value.

In another aspect of the invention, there is a method of determining an analyte concentration in a sample that includes generating an output signal responsive to a concentration of an analyte in a sample and an input signal, determining a compensated value from the output signal in response to a conversion function, a primary function, a first residual function, and a segmented signal processing function, and determining the analyte concentration in the sample from the compensated value. The primary function may include an index function or a complex index function and preferably corrects the error arising from hematocrit levels and temperature or from temperature and total hemoglobin levels in blood samples.

In another aspect of the invention, there is a biosensor system for determining an analyte concentration in a sample that includes a test sensor having a sample interface in electrical or optical communication with a reservoir formed by the sensor and a measurement device having a processor connected to a sensor interface through a signal generator, the sensor interface having electrical or optical communication with the sample interface, and the processor having electrical communication with a storage medium. The processor instructs the signal generator to apply an electrical input signal to the sensor interface, determines an output signal value responsive to the concentration of the analyte in the sample from the sensor interface, and compensates at least 50% of the total error in the output signal value with a primary function. Where if the primary function is not an segmented signal processing function, the processor compensates at least 5% of the remaining error in the output signal with a segmented signal processing function, the segmented signal processing function previously stored in the storage medium, to determine a compensated value, and determines the analyte concentration in the sample from the compensated value. The measurement device of the biosensor system is preferably portable.

In another aspect of the invention, there is a method of determining a segmented signal processing function that includes selecting multiple segmented signal processing parameters as potential terms in the segmented signal processing function, determining a first exclusion value for the potential terms, applying an exclusion test responsive to the first exclusion value for the potential terms to identify one or more of the potential terms for exclusion from the segmented signal processing function, and excluding one or more identified potential terms from the segmented signal processing function.

BRIEF DESCRIPTION OF THE DRAWINGS

The invention can be better understood with reference to the following drawings and description. The components in the figures are not necessarily to scale, emphasis instead being placed upon illustrating the principles of the invention.

FIG. 1B-1 represents a continuous output signal ending in an end-point reading from which the analyte concentration in a sample may be determined.

FIG. 1B-2 represents a gated output signal including the currents measured from three input excitations separated by two relaxations.

FIG. 5A depicts the input signals applied to the test sensor for an electrochemical gated amperometric analysis where six relatively short excitations are separated by five relaxations of varying duration.

FIG. 5B depicts the output current values recorded from the six excitations and the secondary output signal.

DETAILED DESCRIPTION

Analysis error and the resultant bias in analyte concentrations determined from the end-point of a previously continuous output signal may be reduced by segmented signal processing (SSP) of the previously continuous output signal. By dividing the continuous output signal into segments, and converting one or more of the segments into an SSP parameter, an SSP function may be determined. The SSP function may be used singularly or in combination with other functions to reduce the total error in the analysis. The error from the biosensor system may have multiple error sources or contributors arising from different processes/behaviors that are partially or wholly independent.

As SSP compensation arises from the segmenting of an otherwise continuous output signal, the analysis error may be compensated in biosensor systems where compensation based on the output signals from the analyte or analyte responsive measurable species were previously unavailable. Additionally, even in perturbated systems, such as those based on gated amperometry or voltammetry, SSP compensation can implement compensation not dependent on the perturbations arising from the gated input signal.

Residual error compensation may substantially compensate for the total error in an analysis until the error becomes random. Random error is that not attributable to any error contributor and not described by a primary or residual function at a level considered to be statistically significant. An SSP function may provide the primary compensation or the residual compensation to the error correction system. Alternatively the SSP function may be used with a first residual function to provide second residual function compensation to the error correction system. In each of these instances, the SSP function focuses on correcting different error parameters than are compensated by the other compensations.

Figure 1A:
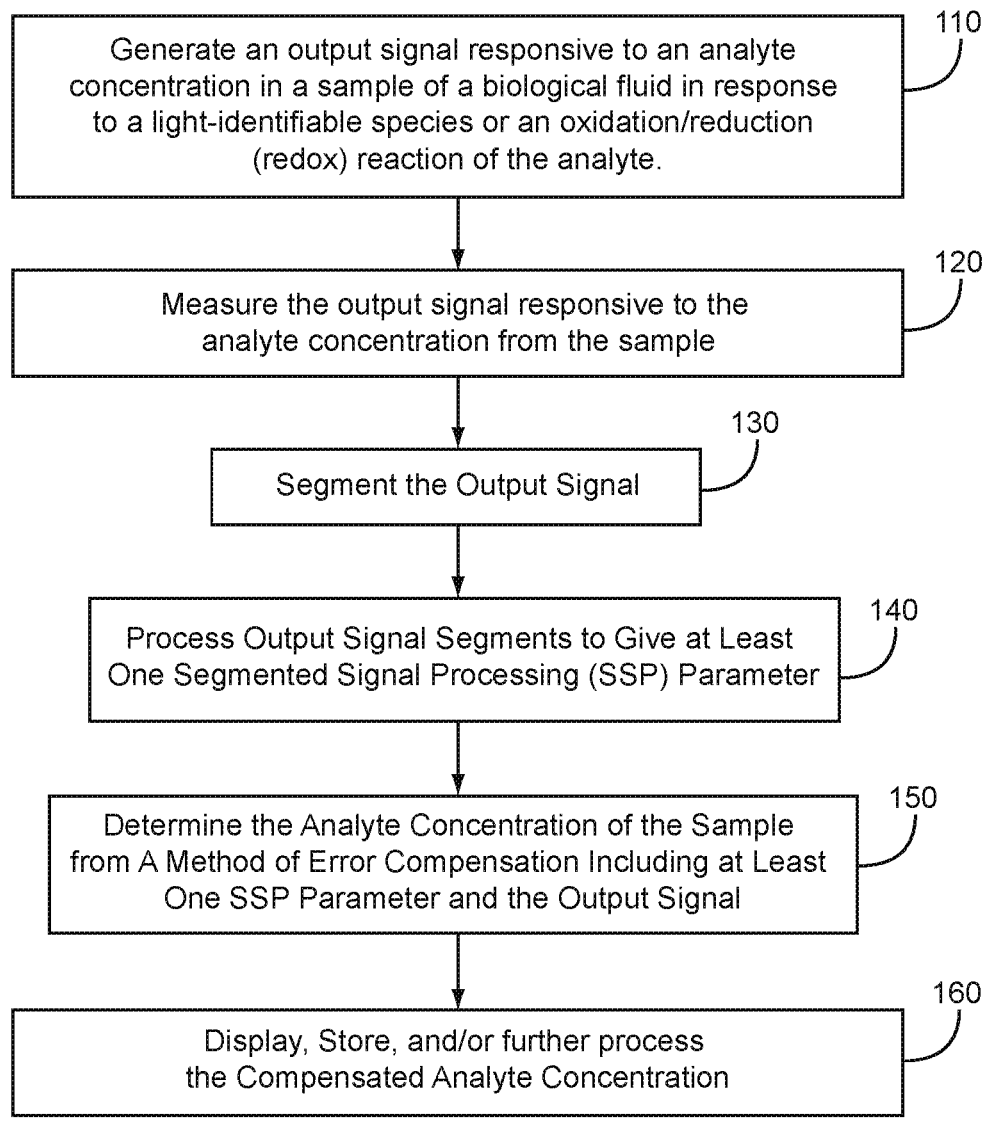
FIG. 1A represents a method for determining an analyte concentration in a sample of a biological fluid using Segmented Signal Processing (SSP).

FIG. 1A represents a method for determining an analyte concentration in a sample of a biological fluid using Segmented Signal Processing (SSP). In 110, the biosensor system generates an output signal responsive to an analyte concentration in a sample of a biological fluid in response to a light-identifiable species or an oxidation/reduction (redox) reaction of the analyte. In 120, the biosensor system measures the output signal responsive to the analyte concentration from the sample. In 130, the biosensor system segments at least a portion of the output signal. In 140, the biosensor system processes one or more of the output signal segments to generate at least one SSP parameter. In 150, the biosensor system determines the analyte concentration from a compensation method including at least one SSP parameter and the output signal. In 160, the compensated analyte concentration may be displayed, stored for future reference, and/or used for additional calculations.

In 110 of FIG. 1A, the biosensor system generates an output signal in response to a light-identifiable species or an oxidation/reduction (redox) reaction of an analyte in a sample of a biological fluid. The output signal may be generated using an optical sensor system, an electrochemical sensor system, or the like.

In 120 of FIG. 1A, the biosensor system measures the output signal generated by the analyte in response to the input signal applied to the sample, such as from a redox reaction of the analyte. The system may measure the output signal continuously or intermittently from continuous or gated excitations. For example, the system may continuously measure the electrical signal from an optical detector responsive to the presence or concentration of an optically active species until an end-point reading is obtained. Similarly, the system may continuously measure the electrical signal from an electrode responsive to the presence or concentration of a redox species until an end-point reading is obtained.

The biosensor system also may measure the output signal continuously or intermittently during the excitations of a gated amperometric or voltammetric input signal, resulting in multiple current values being recorded during each excitation. In this manner, an end-point reading may be obtained at the end of one or more of the multiple input excitations. The biosensor may measure the output signal from the analyte directly or indirectly through an electrochemical mediator. In an optical system, the detector may measure light directly from the analyte or from an optically active species responsive to the concentration of the analyte in the sample to provide the output signal.

An end-point reading is the last operative data point measured for an output signal that has been ongoing. By "last operative" it is meant that while the actual last data point, the second to the last data point, or the third to the last data point, for example, may be used, the end-point reading is the data point reflecting the last state of the analysis for the preceding input signal. Preferably, the end-point reading will be the last data point measured from a specific excitation of the input signal for an electrochemical system. Preferably, the end-point reading will be the last data point measured from the input signal for an optical or other continuous input system.

In 130 of FIG. 1A, the biosensor system segments at least a portion of the output signal. The measurement device of the biosensor system segments at least a portion of the output signal in response to a previously determined segmenting routine. Thus, the output signal values to be measured and represent a particular segment for SSP parameter determination are previously determined before the analysis. Segmenting of the output signal is further discussed below with regard to FIG. 1B.

In 140 of FIG. 1A, the biosensor system processes the output signal values with an SSP parameter processing method to generate at least one SSP parameter. Preferably, at least one SSP parameter is generated from each segment. Generating SSP parameters from the segments of the output signal is further discussed below with regard to FIG. 1C. Unlike compensation systems using one end-point reading to compensate another end-point reading, the SSP parameters originate from values determined before an end-point reading is obtained or before and after an intermediate end-point reading is obtained.

In 150 of FIG. 1A, the biosensor system determines the analyte concentration of the sample from a method of error compensation including at least one SSP parameter and the output signal. The method of error compensation may be slope-based or another method. The at least one SSP parameter may be incorporated into a method of error compensation relying on a conversion function, a method of error compensation relying on a conversion function internalizing a primary compensation, a method of error compensation relying on a distinct conversion function and a distinct primary compensation, and any of these methods of error compensation also including first and/or second residual function compensation. Preferably, a complex index function generated from multiple SSP parameters is used in combination with an output signal value to determine the analyte concentration of the sample. While the SSP parameter is preferably used to compensate during or after the output signal has been converted to an analyte concentration by the conversion function, the SSP parameter could be applied to the output signal before the signal is converted to an analyte concentration.

The SSP function can compensate at least three types of error in the output signal measured from the test sensor. The SSP function may be used to directly compensate the total error present in the output signal when a conversion function is used to convert the output signal into a sample analyte concentration in response to a reference correlation lacking compensation for any error contributors. The SSP function also may be used to compensate when conversion and primary compensation is used to reduce the error attributable to the major error contributors, such as temperature, hematocrit, and hemoglobin. The SSP function also may be used to compensate when conversion, primary compensation, and first residual compensation are used, thus when primary compensation has reduced major error and residual compensation has reduced additional error, such as the user self-testing error. Thus, the SSP function may be considered to compensate relative error in analyte concentrations determined from the sample with conversion and SSP compensation, with conversion, primary compensation, and SSP compensation, or with conversion, primary compensation, residual compensation, and SSP compensation.

Figure 1B:
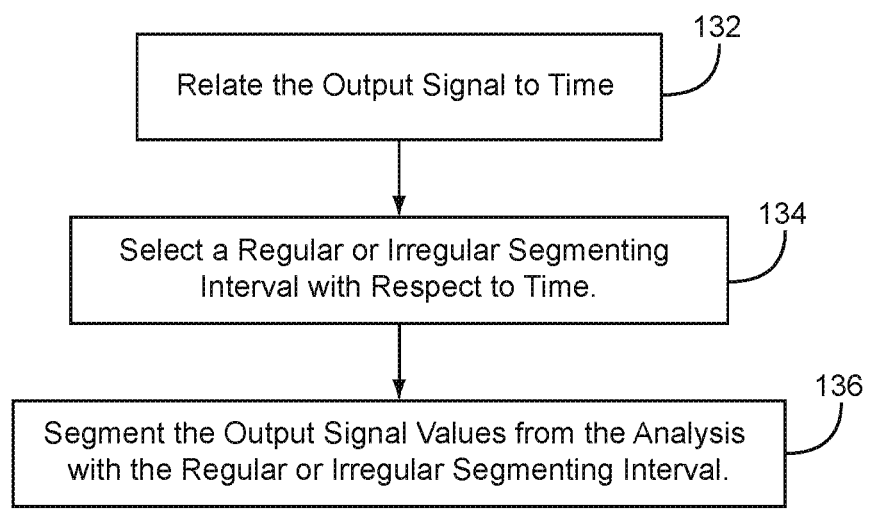
FIG. 1B represents a method of segmenting an output signal.

FIG. 1B represents a method of segmenting an output signal for use in accord with 130 of FIG. 1A. In 132, the output signal is related to time. While time is preferred, another consistently changing metric could be used. In 134, a regular or irregular segmenting interval with respect to time or the other consistently changing metric is chosen. The type of interval selected to segment the output signal is preferably selected based on the portions of the output signal showing the greatest absolute change at a selected time. In 136, the values of the output signal are segmented into individual segments in response to the regular or irregular segmenting interval. Preferably, the output signal is segmented into at least three segments, more preferably at least four. Once the desired segments are determined for the biosensor system, they may be implemented as the segmenting routine in the measurement device. In this manner the measurement device selects which output signal values to assign to which segment for SSP parameter determination.

FIG. 1B-1 represents a continuous output signal ending in an end-point reading from which the analyte concentration in a sample may be determined. In this illustration, the output signal was segmented into output signal segments (a) through (k). Thus, segment (a) is from the time period when the output signal started and segment (k) is from the time period where the end-point reading was made before the analysis was terminated. The end-point reading may be correlated with the analyte concentration of the sample though a linear or non-linear relationship. The output signals may be segmented at regular or irregular intervals with respect to time.

FIG. 1B-2 represents the output signal from a gated amperometric input signal including the currents measured from three input excitations separated by two relaxations. Each excitation ends in an end-point reading from which the analyte concentration or another value relevant to the analysis may be determined. In this illustration, each of the three output signals was segmented into output signal segments (a) through (d). Thus, segment 1a is from the time period when the output signal from the first excitation started and segment 1d is from the time period where the end-point reading for the first excitation was recorded before the first relaxation period. The end-point reading may be correlated with the analyte concentration of the sample or other values relevant to the analysis, such as error parameters, though a linear or non-linear relationship. The output signals may be segmented at regular or irregular intervals with respect to time.

Figure 1C:
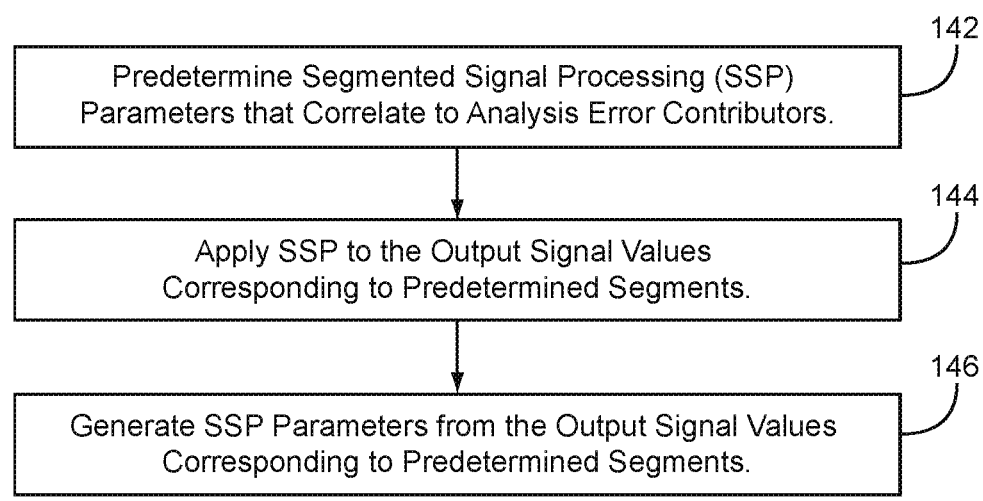
FIG. 1C represents a method of processing output signal segments.

FIG. 1C represents a method of processing output signal segments to provide SSP parameters in accord with 140 of FIG. 1A. In 142, the correlation between one or more SSP parameters and an error contributor of the analysis was previously determined. The correlation may be determined in the laboratory between a potential SSP parameter and error arising from primary error sources, such as hematocrit, temperature, and total hemoglobin in blood samples, or from residual error sources remaining after primary compensation. In 144, segmented signal processing is applied to the output signal values corresponding to one or more predetermined segments. Preferably, the output signal values from at least two segments are processed. More preferably, the output signal values from at least three segments are processed. In 146, an SSP parameter is generated from the output signal values corresponding to the one or more predetermined segments. Preferably, at least two SSP parameter values are generated, more preferably at least three SSP parameters are generated from the one or more predetermined segments.

Any method that converts multiple output values into a single parameter may be used to determine the SSP parameters, however, preferable SSP parameter determining methods include averaging of signals within a segment, determining ratios of the signal values from within a segment, determining differentials of the signal values from within a segment, determining time base differentials, determining normalized differentials, determining time-based normalized differentials, determining one or more decay constants and determining one or more decay rates. For example, the normalized differential method may be implemented by obtaining the differential between the first and the last data point (e.g. current value) for each segment, followed by normalization with the end-point reading of the output signal, or by an intermediate end-point reading of the respective segment or from another segment, for example. Thus, the normalized differential method may be expressed as: (a change in current/the corresponding change in time)/ the end-point selected for normalization. General equations representing of each of these SSP parameter determining methods are as follows:

Averaging of signal values from within a segment: $(Avg)=(i_n+i_m)/2$, where $i_n$ is a first output signal value and $i_m$ is a second output signal value of the segment and where $i_n$ is preferably greater than $i_m$;

Determining ratios of the signal values from within a segment: $(Ratio)=i_m/i_n$;

Determining differentials of the signal values from within a segment: $(Diff)=i_n-i_m$, Determining time-based differentials: Time-based differential $(TD)=(i_n-i_m)/(t_m-t_n)$, where $t_m$ is the time at which the $i_m$ output signal value was measured and $t_n$ is the time at which the $i_n$ output signal value was measured;

Determining normalized differentials: Normalized differential $(Nml\ Diff)=(i_n-i_m)/i_{end}$, where $i_{end}$ is the end-point output signal value of the segment or as described further below;

Determining time-based normalized differentials: Time-based normalized differential $(TnD)=(i_n-i_m)/(t_m-t_n)/i_{end}$;

Determining one or more decay constants: Decay constant $(K)=[\ln(i_n)-\ln(i_m)]/[\ln(t_m)-\ln(t_n)]=\Delta\ln(i)/[-\Delta\ln(t)]$, for a general function relating output signal current values that decay as a function of time to analyte concentration by $i=A*t^K$, where ln represents a logarithmic mathematical operator, "A" represents a constant including analyte concentration information, "t" represents time, and "K" represents the decay constant; and Determining one or more decay rates: Decay rate $(R)=[\ln(i_m)-\ln(i_n)]/(1/t_m-1/t_n)$, for an exponential function of $i=A*\exp(R/t)$, where "exp" represents the operator of the exponential function, and "R" represents the decay rate.

The end-point reading preferably used for normalization is that which is the last current recorded for the excitation being segmented, the last current recorded for the analysis, or the current that correlates best with the underlying analyte concentration of the sample. Other values may be chosen for the normalization value. Normalization preferably serves to reduce the influence of different sample analyte concentrations on the determined SSP parameters.

Figure 1D:
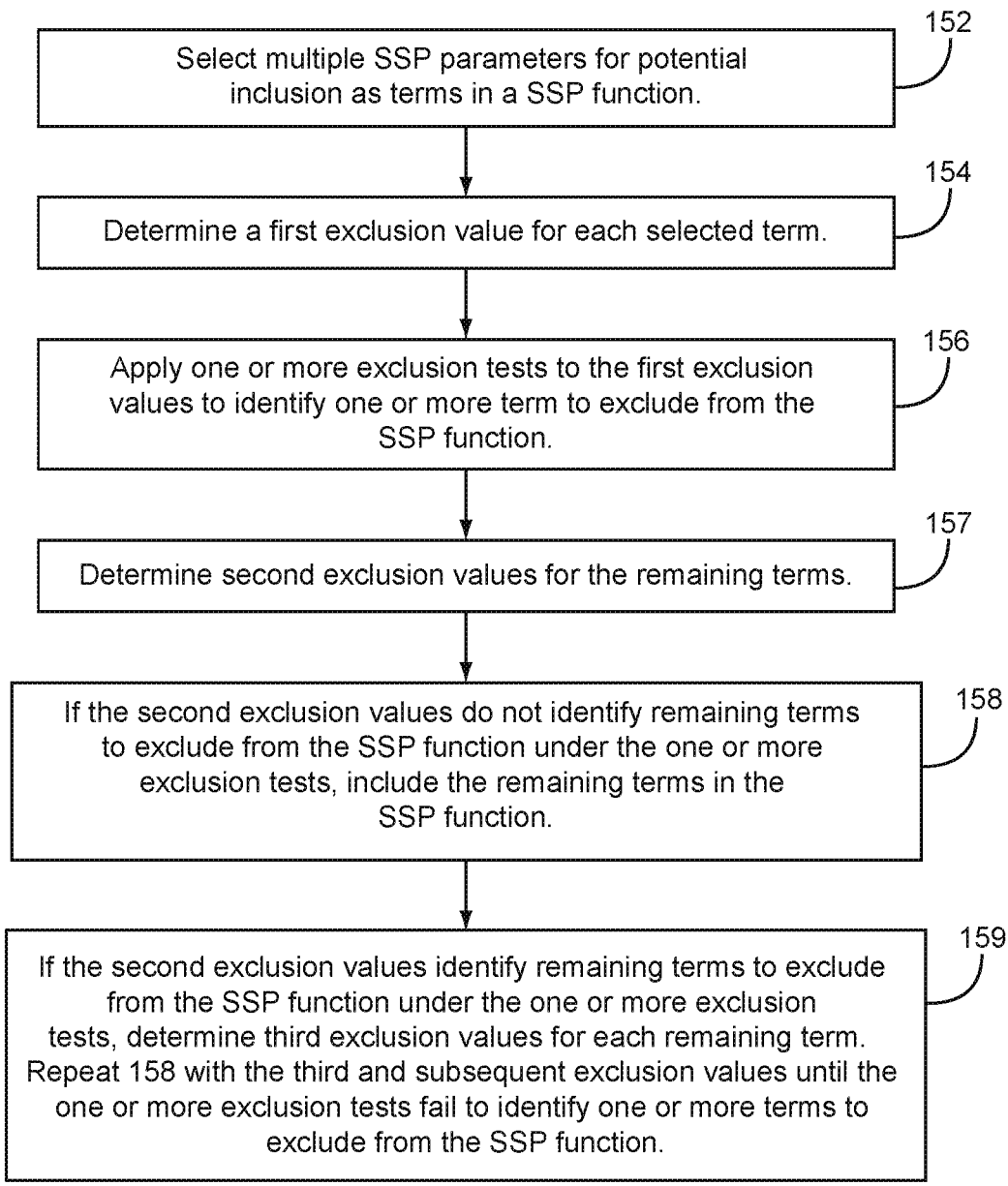
FIG. 1D represents a method for selecting terms for inclusion in a complex index function which may serve as an SSP function.

FIG. 1D represents a method for selecting terms for inclusion in a complex index function which may serve as an SSP function. In 152, multiple SSP parameters are selected as terms for potential inclusion in the complex index function. In addition to the SSP parameters, one or more error or other parameters also may be included in the function. As with the SSP parameters, error parameters may be obtained from an output signal responsive to a light-identifiable species or from the redox reaction of an analyte in a sample of a biological fluid. The error parameters also may be obtained independently from the output signal, such as from a thermocouple. The terms of the complex index function may include values other than SSP and error parameters, including values representing the uncompensated concentration of the analyte in the sample and the like. In 154, one or more mathematical techniques are used to determine first exclusion values for each selected term. The mathematical techniques may include regression, multi-variant regression, and the like. The exclusion values may be p-values or the like. The mathematical techniques also may provide weighing coefficients, constants, and other values relating to the selected terms.

In 156, one or more exclusion tests are applied to the exclusion values to identify one or more terms to exclude from the complex index function. At least one term is excluded under the test. Preferably, the one or more exclusion tests are used to remove statistically insignificant terms from the complex index function until the desired terms are obtained for the function. In 157, the one or more mathematical techniques are repeated to identify second exclusion values for the remaining terms. In 158, if the second exclusion values do not identify remaining terms for exclusion from the complex index function under the one or more exclusion tests, the remaining terms are included in the complex index function. In 159, if the second exclusion values identify remaining terms to exclude from the complex index function under the one or more exclusion tests, the one or more mathematical techniques of 157 may be repeated to identify third exclusion values for the remaining terms. These remaining terms may be included in the complex index function as in 158 or the process may be iteratively repeated as in 159 until the exclusion test fails to identify one or more terms to exclude. Additional information regarding the use of exclusion tests to determine the terms and weighing coefficients for complex index functions may be found in U.S. application Ser. No. 13/053,722, filed Mar. 22, 2011, entitled "Residual Compensation Including Underfill Error".

Figure 2A:
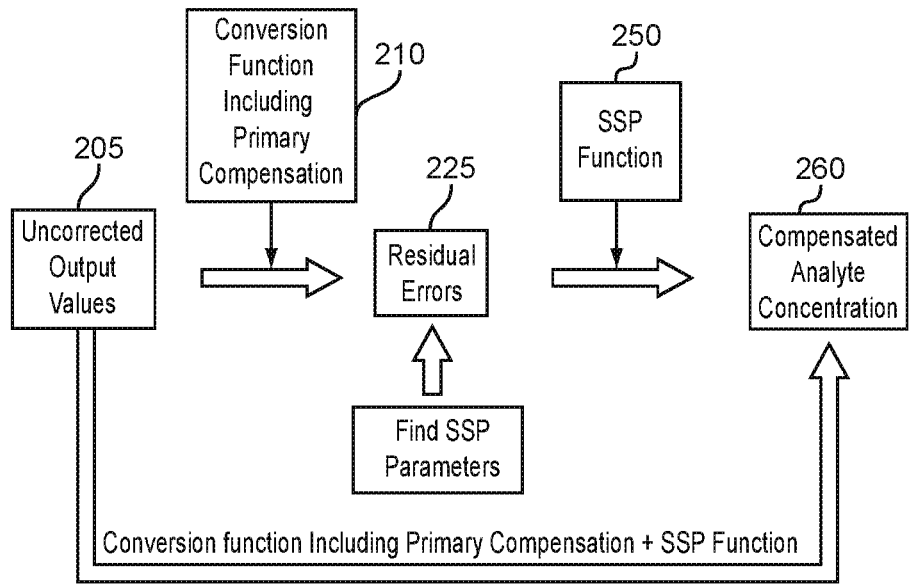
FIG. 2A represents a method of error compensation including a conversion function incorporating primary compensation and SSP parameter compensation.

FIG. 2A represents a method of error compensation including a conversion function incorporating primary compensation 210 and SSP parameter compensation. The output from the conversion function incorporating primary compensation 210 and including residual error 225 is compensated with SSP parameters in the form of an SSP function 250. Thus, the SSP function 250 compensates the uncompensated output values 205 after conversion and primary compensation. The total error 215 includes all error in the analysis, such as random and/or other types of error. The conversion function 210 and the SSP function 250 may be implemented as two separate mathematical equations, a single mathematical equation, or otherwise. For example, the conversion function 210 may be implemented as a first mathematical equation and the SSP function 250 implemented as a second mathematical equation.

In FIG. 2A, uncompensated output values 205 may be output currents responsive to an optical or electrical input signal generating an output signal having a current component. The uncompensated output values may be output signals having a current or potential component responsive to the light detected by one or more detectors of an optical system. The uncompensated output values may be output potentials responsive to potentiometry, galvanometry, or other input signals generating an output signal having a potential component. The output signal is responsive to a measurable species in the sample. The measurable species may be the analyte of interest, a species related to the analyte, an electrochemical mediator whose concentration in the sample is responsive to that of the analyte of interest, or a light-identifiable species whose concentration in the sample is responsive to that of the analyte of interest.

The conversion function 210 is preferably from a predetermined reference correlation between the uncompensated output values 205 generated from a sample in response to an input signal from a measurement device and one or more reference analyte concentrations previously determined for known physical characteristics and environmental aspects of the sample. For example, the conversion function 210 may be able to determine the glucose concentration in a blood sample from the output values 205 based on the sample having a hematocrit content of 42% when the analysis is performed at a constant temperature of 25° C. In another example, the conversion function 210 may be to determine the %-A1c in a blood sample from the output values 205 based on the sample having a specific total hemoglobin content when the analysis is performed at a constant temperature of 23° C. The reference correlation between known sample analyte concentrations and uncompensated output signal values may be represented graphically, mathematically, a combination thereof, or the like. Reference correlations may be represented by a program number (PNA) table, another look-up table, or the like that is predetermined and stored in the measurement device of the biosensor system.

The primary compensation incorporated into the conversion function 210 substantially compensates the major error contributor/s introducing error into the uncompensated output values 205. Thus, in an optical biosensor system that determines the %-A1c in blood, the major error contributors are temperature and total hemoglobin. Similarly, in an electrochemical biosensor system that determines the glucose concentration in blood, the major error contributors are temperature and hematocrit.

The primary function providing the primary compensation may be algebraic in nature, thus linear or non-linear algebraic equations may be used to express the relationship between the uncompensated output values and the error contributors. For example, in a %-A1c biosensor system, temperature (T) and total hemoglobin (THb) are the major error contributors. Similarly to hematocrit error in blood glucose analysis, different total hemoglobin contents of blood samples can result in different A1c signals erroneously leading to different A1c concentrations being determined for the same underlying A1c concentration. Thus, an algebraic equation to compensate these error may be $A1c = a_1 * S_{A1c} + a_2/S_{A1c} + a_3 * THb + a_4 * THb^2$, where A1c is the analyte concentration after conversion of the uncompensated output values and primary compensation for total hemoglobin, $S_{A1c}$ is the temperature compensated output values (e.g. reflectance or adsorption) representing A1c, and THb is the total hemoglobin value calculated by $THb = d_0 + d_1/S_{THb} + d_2/S_{THb}^2 + d_3/S_{THb}^3$, where $S_{THb}$ is the temperature corrected THb reflectance signal obtained from the test sensor. The temperature effects for $S_{A1c}$ and $S_{THb}$ are corrected with the algebraic relationship $S_{A1c} = S_{A1c}(T) + [b_0 + b_1 * (T - T_{ref}) + b_2 * (T - T_{ref})^2]$ and $S_{THb} = [S_{THb}(T) c_0 + c_1 * (T - T_{ref})]/[c_2 * (T - T_{ref})^2]$. By algebraic substitution, the primary compensated analyte concentration A may be calculated with conversion of the uncompensated output values and primary compensation for the major error contributors of temperature and total hemoglobin being integrated into a single algebraic equation.

The primary function also may include a slope-based function, a complex index function, or other compensation function focusing on the reduction of major error, such as temperature and hematocrit or temperature and total hemoglobin, in the analysis. For a slope-based glucose analyte example, the observed total error of a biosensor system including a measurement device and a test sensor may be expressed in terms of $\Delta S/S$ (normalized slope deviation) or $\Delta G/G$ (relative glucose error). Suitable slope-based primary compensation techniques may be found in Intl. Pub. No. WO 2009/108239, filed Dec. 6, 2008, entitled "Slope-Based Compensation" and in Intl. Pub. No. WO 2010/077660, filed Dec. 8, 2009, entitled "Complex Index Functions", for example.

Preferable primary functions that implement slope-based compensation are index functions that may be determined using error parameter values from the analysis of the analyte, such as the intermediate signals from the analyte responsive output signal, or from sources independent of the analyte responsive output signal, such as thermocouples, additional electrodes, and the like. Error parameters may be any value responsive to one or more error in the output signal. Thus, the error parameters may be extracted directly or indirectly from the output signal of the analysis and/or obtained independently from the analytic output signal. Other error parameters may be determined from these or other analytic or secondary output signals. Any error parameter may be used to form the term or terms that make up the index function, such as those described in Intl. Pub. No. WO 2009/108239, filed Dec. 6, 2008, entitled "Slope-Based Compensation," and the like.

An index function is responsive to at least one error parameter. An index function may generate a calculated number that correlates total analysis error to an error parameter, such as hematocrit or temperature, and represents the influence of this error parameter on bias. Index functions may be experimentally determined as a regression or other equation relating the deviation of determined analyte concentrations from a reference slope to the error parameter. Thus, the index function represents the influence of the error parameter on the slope deviation, normalized slope deviation, or percent bias arising from the total error in the analysis.

Index functions are complex when they include combinations of terms modified by term weighing coefficients. A complex index function has at least two terms, each modified by a term weighing coefficient. The combination preferably is a linear combination, but other combination methods may be used that provide weighing coefficients for the terms. For example, a complex index function may have a linear combination of terms with weighing coefficients as follows: f(ComplexIndex)=a1+(a2)(R3/2)+(a3)(R4/3)+(a4)(R5/4)+(a5)(R3/2)(G)+(a6)(R4/3)(G)+(a7)(R3/2)(Temp)+(a8)(R4/3)(Temp)+(a9)(Temp)+(a10)(G)+ . . . , where a1 is a constant and not a weighing coefficient, a2-a10 independently are term weighing coefficients, G is the determined analyte concentration of the sample without compensation, and Temp is temperature. Each of the term weighing coefficients (a2-a10) is followed by its associated term—(R3/2), (R4/3), (R5/4), (R3/2)(G), (R4/3)(G), (R3/2)(Temp), (R4/3)(Temp), (Temp), and (G). Other complex index functions may be used including nonlinear and other combinations of terms with weighing coefficients.

Term weighing coefficients apportion the contribution of each term to the function. Thus, they allow for each term to have a different apportionment to the function. Two or more of the term weighing coefficients may be the same or similarly apportion the contribution of their respective terms to the function. However, at least two weighing coefficients are different or differently apportion the contribution of their respective terms to the function. In this way, the term weighing coefficients may be selected to allow for the effect of one term on another term in relation to the overall function, thus reducing or eliminating error from the interactions of the terms when the complex index function is used. The term weighing coefficients may have any value, preferably numerical values other than one or zero, as a weighing coefficient of 1 may not apportion the contribution of the term and a weighing coefficient of 0 would result in the exclusion of the term. The term weighing coefficients are not a single value or constant that may be applied by algebraic disposition to all the terms. Term weighing coefficients may be determined through the statistical processing of the data collected from a combination of multiple analyte concentrations, different hematocrit levels, different total hemoglobin levels, different temperatures, and the like.

Additionally, a complex index function is not only a "complex function" in a mathematical sense, thus requiring or implying the use of an imaginary number (a number with the square root of negative one). A complex index function may include one or more imaginary numbers, such as one of the terms or weighing coefficients, but is not limited or restricted to having any imaginary numbers.

Each term in a complex index function may include one or more error parameters. The terms may be selected with one or more exclusion tests. More preferably, primary functions are complex index functions, such as those described in Intl. Pub. No. WO 2010/077660, filed Dec. 8, 2009, entitled "Complex Index Functions". Other primary compensation techniques may be used.

The residual error 225 may be expressed generally by Residual Error=total error observed−primary function corrected error. The residual error 225 remaining in the analyte concentration not compensated by the primary function may be considered to arise from operating condition, manufacturing variation, and/or random error. Of the total error in the uncompensated output values 205, primary compensation removes at least 40% of this error from the compensated analyte concentration 225, preferably at least 50%. Preferably, primary compensation removes from 40% to 75% of the total error in the uncompensated output values, and more preferably from 50% to 85%.

Figure 2B:
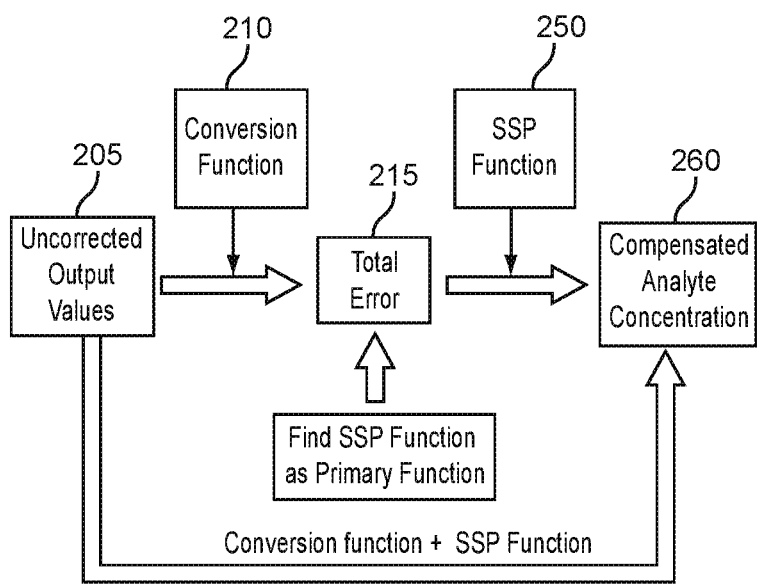
FIG. 2B represents a method of error compensation including a conversion function and SSP parameter compensation.

FIG. 2B represents a method of error compensation including a conversion function 210 and SSP parameter compensation. The output from the conversion function 210 including total error 215 is compensated with SSP parameters in the form of a SSP function 250 to provide primary compensation. Thus, the SSP function 250 compensates the uncompensated output values 205 after conversion. The total error 215 includes primary and residual error. The total error 215 also may include random and/or other types of error. The conversion function 210 and the SSP function 250 may be implemented as two separate mathematical equations, a single mathematical equation, or otherwise. For example, the conversion function 210 may be implemented as a first mathematical equation, and the SSP function 250 implemented as a second mathematical equation.

In FIG. 2B, the conversion function 210 and the uncompensated output values 205 may be considered similar to those discussed with regard to FIG. 2A, except that the conversion function 210 does not internalize primary compensation. When the sample is blood and the analyte is glucose, the compensation provided by the SSP function 250 may be substantially limited to compensation for analysis error arising from temperature and/or hematocrit. Thus, by characterizing the biosensor system with respect to temperature and/or hematocrit change, the effects from temperature and/or hematocrit may be compensated by the SSP function 250.

Figure 2C:
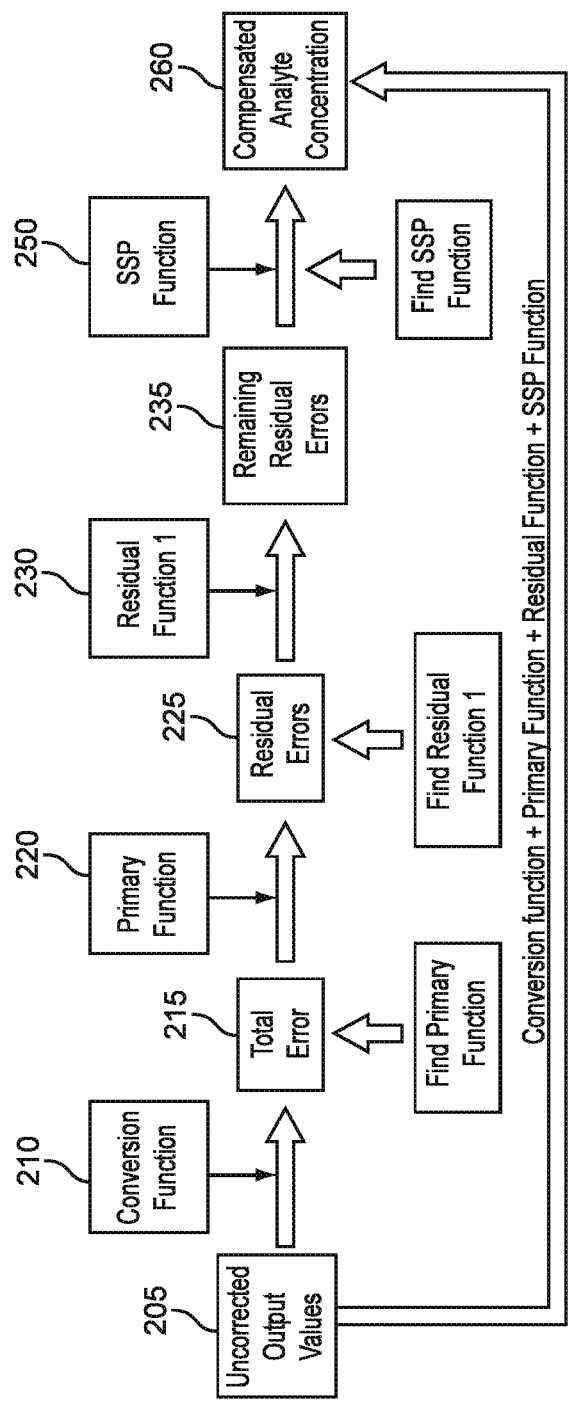
FIG. 2C represents a method of error compensation including a conversion function, primary compensation, first residual compensation, and second residual compensation provided by SSP parameter compensation.

FIG. 2C represents a method of error compensation including a conversion function 210, primary compensation, first residual compensation, and second residual compensation provided by SSP function compensation. The output from the conversion function 210 including total error 215 is compensated with a primary compensation in the form of a primary function 220. The remaining residual error 225 is compensated with a residual compensation in the form of a first residual function 230 responsive to user self-testing error. The remaining residual error 235 is compensated with SSP parameters in the form of a SSP function 250. Thus, the SSP function 250 compensates the uncompensated output values 205 after conversion, primary compensation, and first residual compensation. The total error 215 includes primary and residual error. The total error 215 also may include random and/or other types of error. The conversion function 210, the primary function 220, the first residual function 230, and the SSP function 250, which serves as a second residual function in this example, may be implemented as four separate mathematical equations, a single mathematical equation, or otherwise. For example, the conversion function 210 may be implemented as a first mathematical equation, while the primary function 220, the first residual function 230, and the SSP function 250 are combined and implemented as a second mathematical equation.

In FIG. 2C, the conversion function 210 and the uncompensated output values 205 may be considered similar to those discussed with regard to FIG. 2A. The primary function 220 may be considered a complex index function implementing a slope-based compensation, as previously discussed. The first residual function 230 providing at least a portion of the residual compensation is applied in addition to compensating the major error with the primary function 220.

The observed residual error substantially lacked the error removed from the total error by the values of the primary function 220. The total error includes error from substantially different sources and/or test cases, such as temperature and hematocrit error determined in a controlled environment (substantially described by the primary function), versus operating condition error originating from outside of a controlled environment (substantially described by the residual function) and manufacturing variation. By focusing on the residual error in a particular situation, such as user self-testing by inexperienced subjects, and finding at least one residual function associated with the residual error, the measurement performance of the biosensor system may be improved. Residual error remaining after application of the first residual function 230 may be further reduced with the application of a second residual function in the form of a SSP function 250.

In this example, while the error described by the SSP function may be from either a controlled environment or a non-controlled environment, the error is preferably non-random error from a non-controlled environment remaining after use of a conversion function including primary compensation, a conversion function plus primary compensation, and/or error remaining after use of a conversion function plus primary and first residual function compensation. The second residual function may be selected to compensate systematic deficiencies in the compensation provided by the primary or primary and first residual functions. Preferably, the error corrected by the SSP function shows a lower correlation with the primary and/or first residual functions than with the SSP function.

In addition to including primary compensation, first residual compensation, and at least one SSP compensation, the method of error compensation represented in FIG. 2C may include the ability to adjust the compensation provided by the primary compensation in relation to the compensation provided by the residual compensation in relation to the compensation provided by the SSP compensation. The residual compensation also may include the ability to adjust the compensation provided by the first residual function in relation to the compensation provided by the SSP function.

The error compensation provided by the primary compensation in relation to the compensation provided by the residual and SSP compensations may be adjusted because the function or functions making up the first residual compensation may be taken from predetermined values stored in the measurement device as a database or otherwise for a limited temperature and/or hematocrit range, while the primary and SSP functions may be determined from a full range of sample temperature and hematocrit content. Thus, the primary and SSP functions may be determined from inputs acquired during the analysis of a sample, while a finite number of first residual functions may be predetermined and stored in the measurement device. The error compensation provided by the primary and SSP compensations in relation to the compensation provided by the first residual compensation also may be adjusted because some overlap may occur between the error described by the primary, the SSP, and one or more residual functions. There may be other reasons to adjust the error compensation provided by the primary and SSP compensations in relation to the compensation provided by the residual compensation.

One method of adjusting the error compensation provided by the primary and SSP compensations in relation to the compensation provided by the first residual compensation includes the use of function weighing coefficients. Compensation in a general form, where the error compensation provided by the primary and SSP compensations is adjusted in relation to the compensation provided by the residual compensation, may be expressed as: Primary function+$WC1$*Residual function+$WC2$*SSP function, where $WC1$ and $WC2$ are the function weighing coefficients for the two compensation types. The function weighing coefficient WC may be selected as a function of temperature and/or hematocrit for varying compensation contributions from the first residual function and the SSP function. Similarly, compensation including one or more residual functions and an SSP function where the residual functions are each modified by a function weighing coefficient may take the following general forms:

Compensated analyte concentration=current nA/(Slope$_{Cal}$*(1+primary function+$WC1$*residual1+$WC2$*residual2 . . . +$WC3$*SSP function)), or using the alternative general form of residual:

Compensated analyte concentration=current nA/(Slope$_{Cal}$*(1+primary function)*(1+$WC1$*residual1)*(1+$WC2$*residual2) . . . *(1+$WC3$*SSP function), where $WC1$, $WC2$, and $WC3$ are function weighing coefficients having values between 0 and 1 and allow the effect of the residual function/s and SSP function to be reduced when conditions are outside those that were used to develop the residual function. While similar in operation to the term weighing coefficients previously discussed, function weighing coefficients apportion the contribution of each compensation function to the total compensation in response to the total error.

Residual1 is the first level of residual compensation after the primary compensation function, while Residual2 is the next level of residual compensation, but may not be available if an error source/index function is not found. Residual1 and Residual2 are preferably independent of each other and of the primary function. Preferably, the SSP function is independent of the primary and residual functions.

Function weighing coefficients for the primary, versus first residual compensation, versus SSP compensation may be predetermined and stored in the measurement device in the form of a table or through other means. For example, the $WC1$, $WC2$, and $WC3$ values may be characterized in a two-dimensional table as a function of temperature and hematocrit. In this way, the function weighing coefficient table may be structured to improve the measurement performance of the biosensor system by reducing the effect of the residual function or functions on the determined analyte concentration when the hematocrit content of the sample and the temperature at which the analysis is performed are relatively close to the conditions under which the data was obtained that was used to determine the conversion function 210. Additional information addressing residual compensation and weighing coefficients may be found in U.S. application Ser. No. 13/053,722, filed Mar. 22, 2011, entitled "Residual Compensation Including Underfill Error".

Biosensor systems having the ability to generate additional output values external to those from the analyte or from the mediator/light-identifiable species responsive to the analyte also may benefit from the previously described methods of error compensation. Systems of this type generally use the additional output value or values to compensate for interferents and other contributors by subtracting the additional output value or values from the analyte responsive output signal in some way. Error parameters may be extracted directly or indirectly from the output signal of the analysis and/or obtained independently from the output signal. Thus, the additional output values external to those from the analyte or from the mediator responsive to the analyte may be used to form terms, such as those described in Intl. Pub. No. WO 2009/108239, filed Dec. 6, 2008, entitled "Slope-Based Compensation," and the like.

Figure 3A:
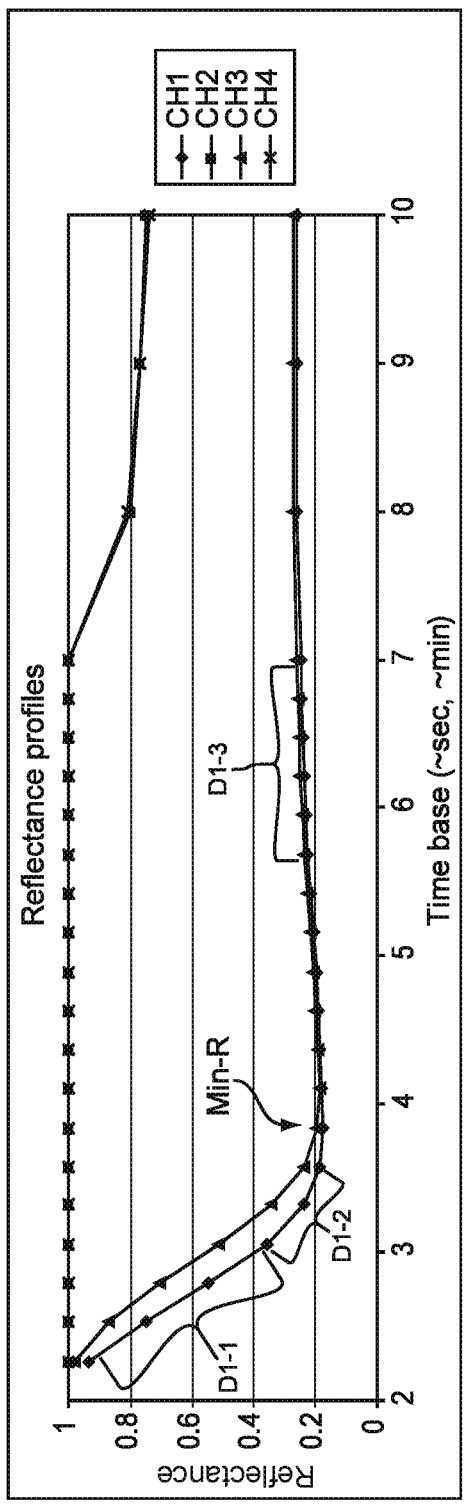
FIG. 3A and FIG. 3B depict the output signals in the form of reflectance as a function of time from an optical laminar flow system where two channels of chemical reaction and optical detection perform the same analysis to increase accuracy.
Figure 3B:
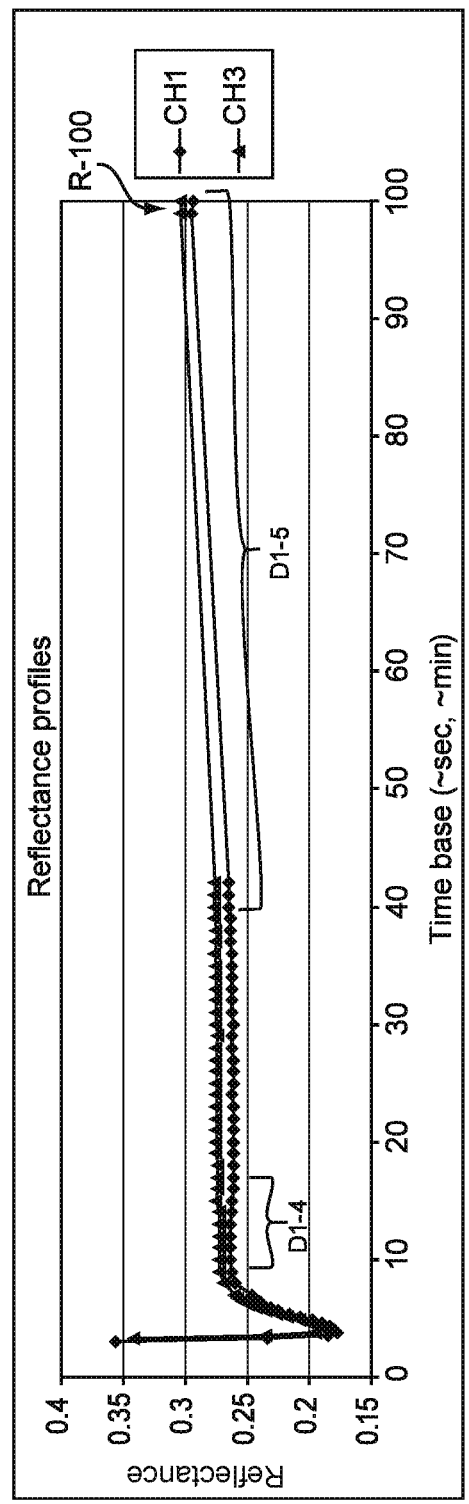

FIG. 3A and FIG. 3B depict the output signals in the form of reflectance as a function of time from an optical laminar flow system where two channels of chemical reaction and optical detection perform the same analysis to increase accuracy. Each detection channel detects both A1c and total hematocrit (THb) reflectance signals. FIG. 3A shows the typical response of reflectance profile for channels 1 and 2, and 3 and 4, respectively from two separate strips within the laminar flow test sensor. Channels 1 and 3 are the A1c reflectance output signals, while channels 2 and 4 are the total hemoglobin reflectance output signals. FIG. 3B shows a longer time base for channels 1 and 3. Having an end-point signal for each channel, SSP was applied to the continuous reflectance profile for each channel. The output signal (A1c reflectance profile) was segmented into five segments, which are designated as D1-1, D1-2, D1-3, D1-4 and D1-5 for the channel 1 A1c reading spot (CH1) and D3-1, D3-2, D3-3, D3-4 and D3-5 for the channel 3 A1c reading spot (CH3).

The plots show two segments before the minimum reflectance (Min-R) (D1-1 and D1-2), one immediately after Min-R (D1-3), one in the beginning stage of approaching a steady state (D1-4), and one representing the last stage toward the end-point signal R−100 (D1-5). The output signals were segmented and processed using a time based differential, $\Delta R/\Delta t$, which is unit-less. Other methods of segmenting and processing the output signals may be used.

In FIG. 3A and in FIG. 3B, the x-axis is expressed in numerical values internalizing time because of the irregular data acquisition interval. Before and right after Min-R, the time unit is 0.3 seconds per ~0.25. While after Min-R has past, each numerical value represents 3 seconds, which leads to 300 seconds at the end-point reading R−100. Thus, for the time base numbers 2 through 7 on the x-axis, each number includes 4 data points separated by 0.3 seconds (4 data points are included between 2 and 3 along the x-axis). Similarly, for the time base numbers 7 to 42 on the x-axis, 1 data is point, separated by 3 seconds, is included per time base number. With regard to the actual length of the analysis, the time base number 10 on the x-axis of FIG. 3A represents about 30 seconds having passed since the start of the analysis. In FIG. 3B, the time base number 40 on the x-axis represents approximately 120 seconds having passed since the start of the analysis, and the time base number 40 represents the passage of approximately 300 seconds since the start of the reaction.

The output signal segments were then processed to provide SSP parameters and their cross-terms and then considered as terms for potential inclusion in the complex index function, which served as the SSP function. Table 1, below, lists the weighing coefficients selected in view of the exclusion test/s resulting from a multi-variable regression of SSP parameters and cross-terms that combine an SSP parameter with an additional value. MINITAB version 14 software was used with the Multi-Variant Regression of Linear Combinations of Multiple Variables option chosen to perform the multi-variable regression. Other statistical analysis or regression options may be used to determine the weighing coefficients for the terms.

TABLE 1

Results of optical multivariable regression from output signal of channel 1.

| Terms | Weighing Coefficients |
|---|---|
| Temp | 0.032659 |
| MR1 | 1.3669 |
| D1-1*A1 | 0.13053 |
| D1-3*A1 | 1.3798 |
| D1-4*A1 | −3.1767 |
| D1-5*A1 | −170.02 |
| D3-1*A3 | 0.24341 |
| D3-2*A3 | 0.26661 |
| D3-3*A3 | −0.20696 |
| D1-1*A3 | −0.12288 |
| D1-5*A3 | 114.50 |
| D3-1*A1 | −0.24499 |
| D3-2*A1 | −0.28015 |
| A1Mt1D1-3 | −0.48557 |
| A1Mt1D1-5 | 29.822 |
| Mt1*D1-3 | 1.4891 |
| Mt1*D1-5 | −166.94 |

The resulting complex index function which served as the SSP function for channel 1 may be represented as follows:

SSP Function $CH1 = -0.88664 + 0.03266*'T'+ 1.367*'MR1'+0.1305*'D1-1*A1'+1.3798*'D1-3*A1'-3.177*'D1-4*A1'-170*'D1-5*A1'+ 0.2434*'D3-1*A3'+0.2666*'D3-2*A3'- 0.207*'D3-3*A3'-0.1229*'D1-1*A3'+ 114.5*'D1-5*A3'-0.245*'D3-1*A1'- 0.2802*'D3-2*A1'-0.4856*'A1Mt1D1-3'+ 29.82*'A1Mt1D1-5'+1.489*'Mt1*D1-3'- 166.9*'Mt1*D1-5'$ where −0.88664 is a constant, T is temperature, MR1 is the reflectance at the minimum reflectance (Min-R) from channel 1, A1 is A1c concentration determined from channel 1 using the conversion function internalizing primary compensation, A3 is the A1c value from channel 3, D1-1 through D1-5 are the SSP parameters from output signal segments D1-1 through D1-5 in FIG. 3A, and Mt1 is the time at which the Min-R reflectance was recorded from channel 1.

Figure 3C:
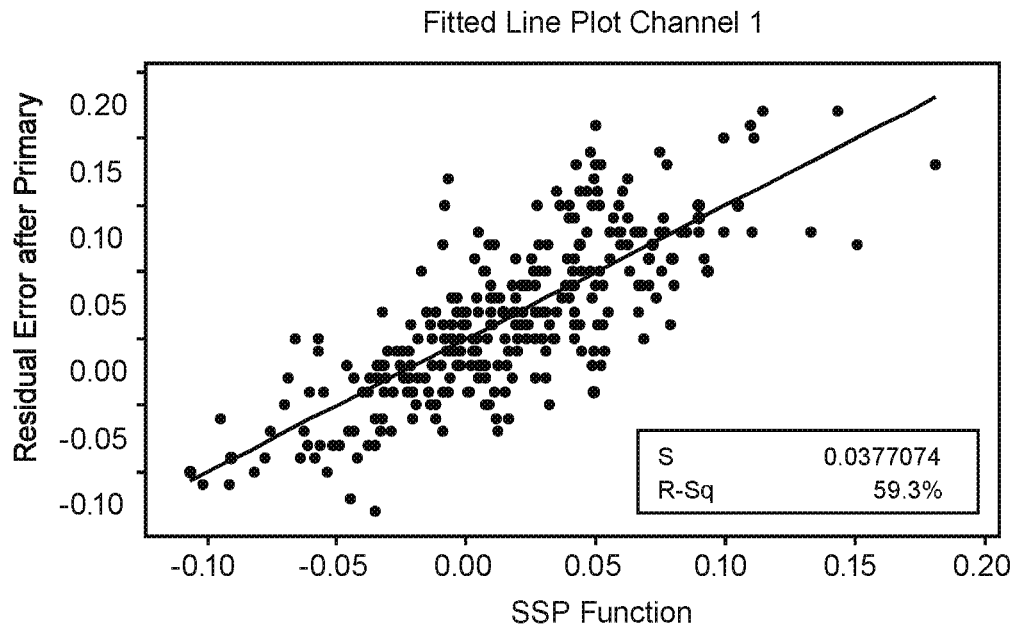
FIG. 3C shows the correlation plot relating residual error after conversion and primary compensation to the ability of the SSP function to describe the residual error in relation to the reference %-A1c concentration of the samples for channel 1.

FIG. 3C shows the correlation plot relating residual error after conversion and primary compensation to the ability of the SSP function to describe the residual error in relation to the reference %-A1c concentration of the samples for channel 1. Thus, the SSP function for channel 1 was able to describe nearly 60% ($R^2=59.3$) of the error remaining after the uncompensated output values were converted and primary compensation was applied to compensate for temperature and total hemoglobin error. Preferably, the SSP function will describe at least 50% of the residual error remaining after application of the conversion and primary compensation functions to the uncompensated output values from the test sensor.

A similar process was repeated for the output signal from channel 3. The results are presented in Table 2, below.

TABLE 2

Results of optical multivariable regression from output signal of channel 3.

| Terms | Weighing Coefficients |
|---|---|
| Temp | 0.028506 |
| D1-1*A1 | 0.18950 |
| D1-2*A1 | 0.14789 |
| D1-5*A1 | −38.919 |
| D3-3*A3 | 1.2120 |
| D3-5*A3 | −194.99 |
| D1-1*A3 | −0.18606 |
| D1-2*A3 | −0.14913 |
| D1-4*A3 | −4.4662 |
| D3-2*A1 | −0.038527 |
| D3-5*A1 | 165.77 |
| A3MR3D3-3 | −5.757 |
| A3MR3D3-5 | 501.29 |
| A3MRt3D3-5 | −8.354 |
| Mt3*D3-2 | 0.031573 |
| Mt3*D3-4 | 3.4435 |

Figure 3D:
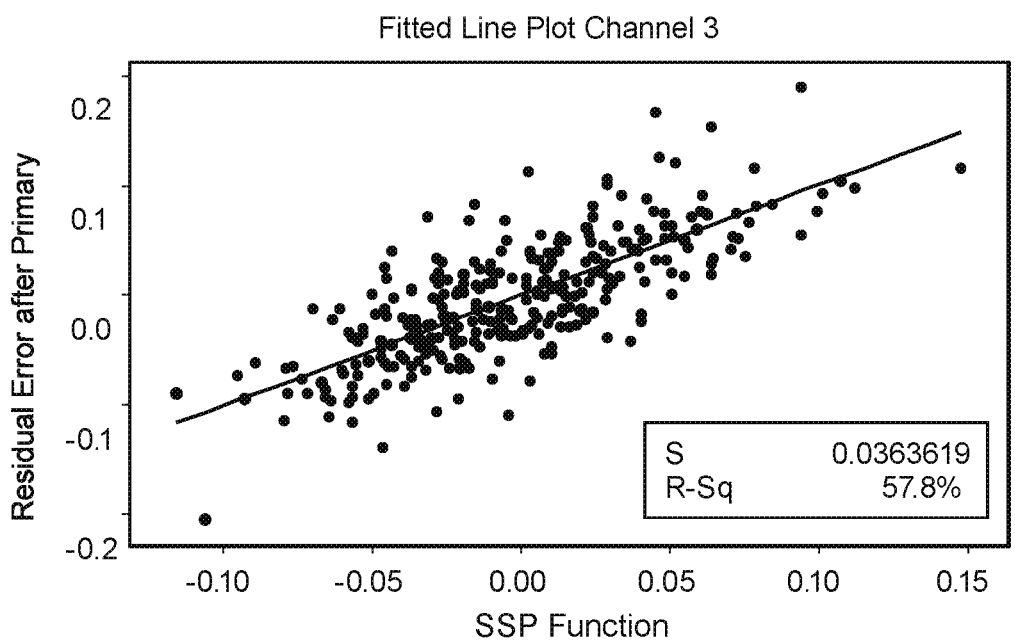
FIG. 3D shows the correlation plot relating residual error after conversion and primary compensation to the ability of the SSP function to describe the residual error in relation to the reference %-A1c concentration of the samples for channel 3.

The resulting complex index function which served as the SSP function for channel 3 may be represented as follows:

SSP Function $CH3 = -0.68117 + 0.02851*'T' + 0.1895*'D1\text{-}1*A1' + 0.14789*'D1\text{-}2*A1' - 38.919*'D1\text{-}5*A1' + 1.212*'D3\text{-}3*A3' - 195*'D3\text{-}5*A3' - 0.18606*'D1\text{-}1*A3' - 0.14913*'D1\text{-}2A3' - 4.4662*'D1\text{-}4A3' - 0.038527*'D3\text{-}2*A1' + 165.77*'D3\text{-}5*A1' - 5.757*'A3MR3D3\text{-}3' + 501.29*'A3MR3D3\text{-}5' - 8.354*'A3MRt3D3\text{-}5' + 0.031\,573*'Mt3*D3\text{-}2' + 3.4435*'Mt3*D3\text{-}4'$ FIG. 3D shows the correlation plot relating residual error after conversion and primary compensation to the ability of the SSP function to describe the residual error in relation to the reference %-A1c concentration of the samples for channel 3. Again, the SSP function for channel 3 was able to describe nearly 60% ($R^2 = 57.8$) of the error remaining after the uncompensated output values were converted and primary compensation was applied. Both the SSP CH1 and CH3 functions were the compensation functions representing the relative errors of channels 1 and 3 $(\Delta A1c/A1c)_1$, $(\Delta A1c/A1c)_3$. Compensation was carried out as follows: $A1c_{comp1} = A1c_{raw1}/(1+SSP1)$ and $A1c_{comp3} = A1c_{raw1}/(1+SSP3)$. The final A1c value was determined with the general relationship $A1c_{final} = (A1c_{comp1} + A1c_{comp3})/2$, and was the average from channels 1 and 3.

Figure 3E:
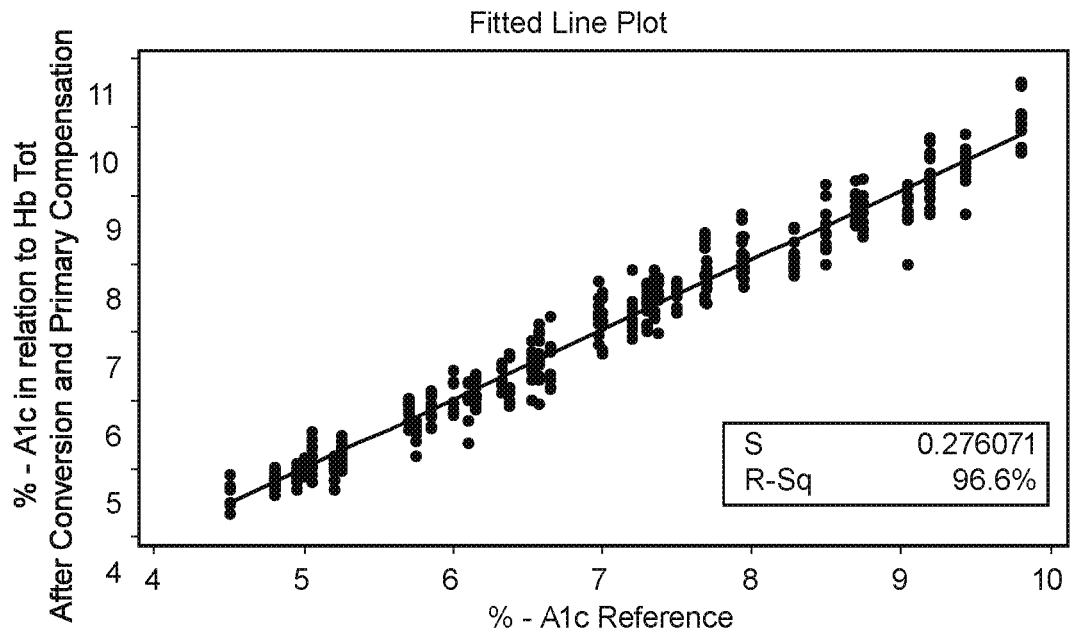
FIG. 3E and FIG. 3F compare the results from the analysis with using a conversion and an internalized algebraic primary compensation with the compensated analyte concentration after use of the SSP function in addition to the internalized algebraic primary compensation.
Figure 3F:
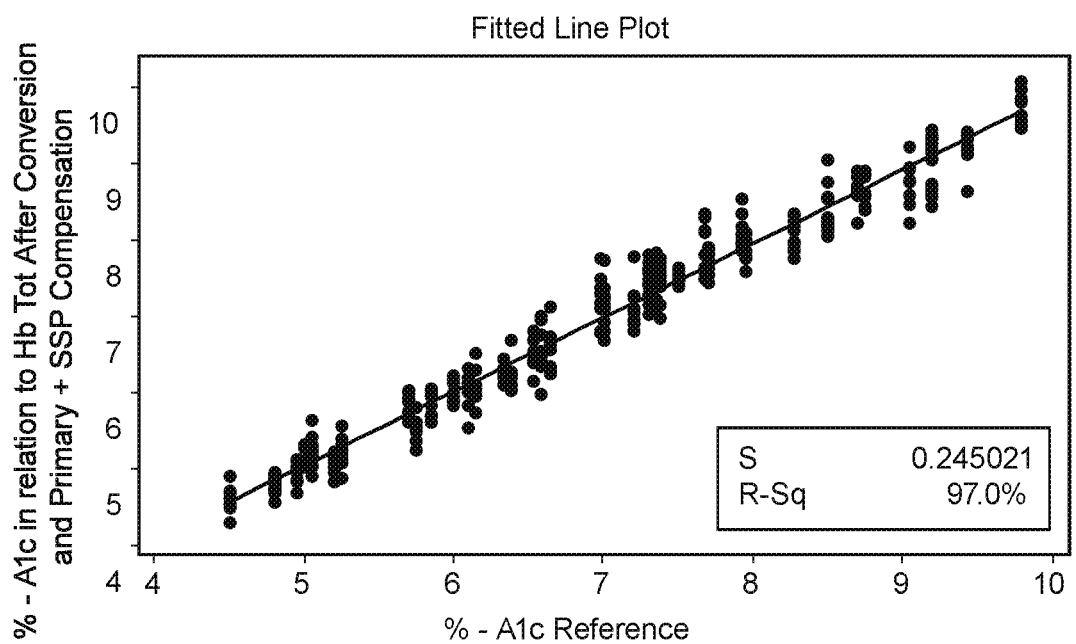

FIG. 3E and FIG. 3F compare the results from the analysis using a conversion function with an internalized algebraic primary compensation verses using the same conversion function with internalized primary compensation and the addition of SSP function compensation. Five different lots of test sensors were used for the analyses and their data combined. The improvement in the percent bias standard deviation between the analyses provided by the SSP function was about 10%, with an additional improvement in measurement performance arising from the mean percent bias moving closer to zero (−0.011 vs. 0.043). Preferably, the SSP function provides an at least 5%, more preferably an at least 8%, improvement in the percent bias standard deviation for five different lots of test sensors.

Table 3, below, summarizes the individual lot performances. For each lot of test sensors, an improvement in measurement performance arises from the reduction in percent bias standard deviation, the mean percent bias moving closer to zero, or both.

TABLE 3

Measurement performance of individual test sensor lots

| | | Lot#1 | Lot#2 | Lot#3 | Lot#4 | Lot#5 | Overall |
|---|---|---|---|---|---|---|---|
| Conversion + Primary | Mean % bias | 0.049 | 0.029 | 0.062 | 0.111 | −0.039 | 0.042 |
| | % bias SD | 0.332 | 0.258 | 0.317 | 0.238 | 0.215 | 0.276 |
| Conversion + Primary + SSP | Mean % bias | −0.044 | −0.056 | 0.068 | −0.002 | −0.019 | −0.011 |
| | % bias SD | 0.299 | 0.225 | 0.261 | 0.242 | 0.190 | 0.246 |

Figure 4A:
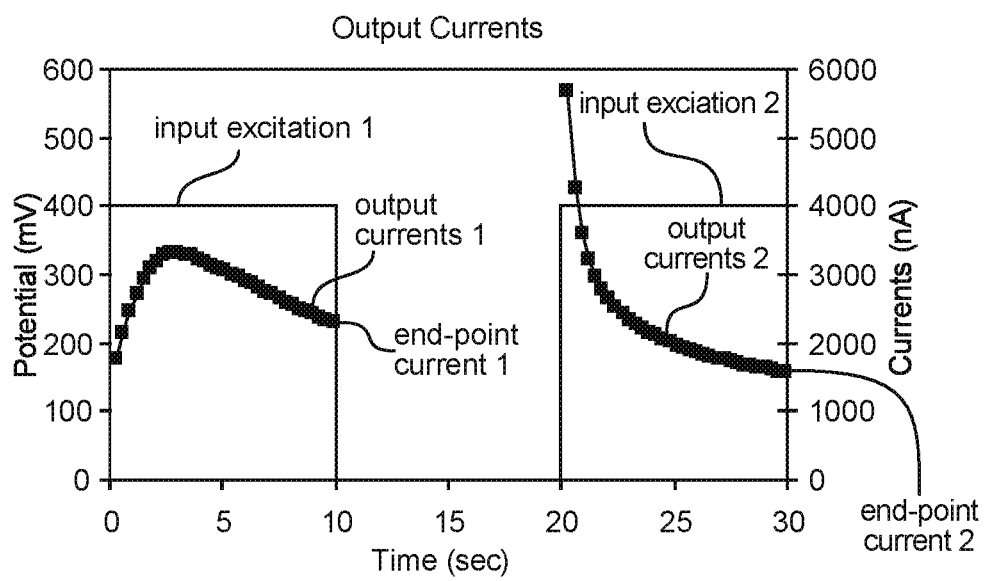
FIG. 4A depicts the output signals from an electrochemical amperometric analysis when two relatively long excitations separated by a relatively long relaxation are applied to a sample of blood containing glucose.

FIG. 4A depicts the output signals from an electrochemical amperometric analysis when two relatively long excitations separated by a relatively long relaxation are applied to a sample of blood containing glucose. Such an analysis may be performed on a blood sample using a measurement device and a test sensor. The sample of blood included 100 mg/dL of glucose and included 40% (weight/weight) hematocrit. The first excitation of the input signal generated output currents 1, while the second excitation of the input signal generated output currents 2. The first excitation is not used to determine the concentration of the analyte (glucose) in the sample (blood), but primarily functions to oxidize mediator that has undergone reduction during storage of the test sensor. The final current of the output currents 2 (at 30 seconds) is the end-point reading and is used with a conversion function to determine the analyte concentration of the sample. The analysis was performed at approximately 25° C.

Figure 4B:
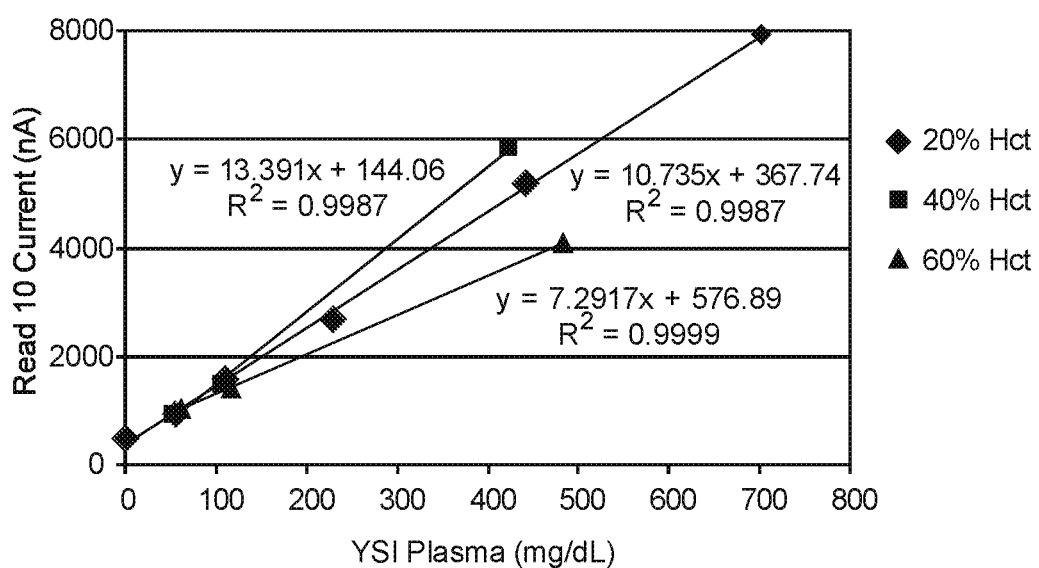
FIG. 4B shows the dose response lines when this analysis was performed on multiple blood samples at approximately 25° C., but with hematocrit contents of 20%, 40%, and 60% and glucose concentrations from 0 to 700 mg/dL.

FIG. 4B shows the dose response lines when this analysis was performed on multiple blood samples at approximately 25° C., but with hematocrit contents of 20%, 40%, and 60% and glucose concentrations from 0 to 700 mg/dL. For each analysis, the analyte concentration of the sample was directly determined from the end-point reading of the second excitation, thus at 30 seconds in relation to FIG. 4A. As may be seen in the divergence between the lines, the hematocrit effect can result in up to ±30% bias verses the reference concentration as determined with a YSI reference instrument in plasma.

The output currents from the first and second excitations were segmented. The output currents from the first excitation were divided into the following segments:

Segment 1 (designated as "0.9"): data points 1 through 3. These data points were measured within 0.9 seconds of the application of the input signal to the sample, with a data point measured at 0.3 second intervals. This Segment included a total of 3 data points.

Segment 2 (designated as "1.8"): data points 4 through 6. Data point 1.8 represents the $6^{th}$ data point measured and is the last data point included in this segment. Thus, Segment 2 includes data points recorded after the 0.9 second recorded data point (which is included in Segment 1) up to and including the data point recorded at 1.8 seconds from the initial application of the input signal to the sample. This Segment included a total of 3 data points.

Segment 3 (designated as "2.7"): data points 7 through 9. This Segment included a total of 3 data points.

Segment 4 (designated as "3.6"): data points 10 through 12. This Segment included a total of 3 data points.

Segment 5 (designated as "4.8"): data points 13 through 16. This Segment included 4 data points.

Segment 6 (designated as "6"): data points 17 through 20. This Segment included 4 data points.

Segment 7 (designated as "7.2"): data points 21 through 24. This Segment included 4 data points.

Segment 8 (designated as "8.4"): data points 25 through 28. This Segment included 4 data points.

Segment 9 (designated as "9.9"): data points 30 through 33. This Segment included 4 data points.

An irregular segmenting interval was used to segment the output signals from the two input excitations. The segmenting interval started at 0.9 second (Segment 1 to Segment 4), increased to 1.2 second (Segment 5 to Segment 8), and ended with a 1.5 second interval (Segment 9). As the decay in the output signal currents became shallower, a relatively longer segmenting interval was used to provide better definition to the resulting SSP parameters. Thus, segmenting intervals that increase the definition between the SSP parameters are preferred.

As the first excitation is not used to determine the concentration of the analyte in the sample, the second excitation was segmented and processed similarly to a continuous output signal as previously described. The output currents from the second excitation were similarly divided into the following segments: 20.9, 21.8, 22.7, 23.6, 24.8, 26, 27.2, 28.4 and 29.9. The same irregular segmenting intervals were used to segregate the output currents from the second excitation.

Figure 4C:
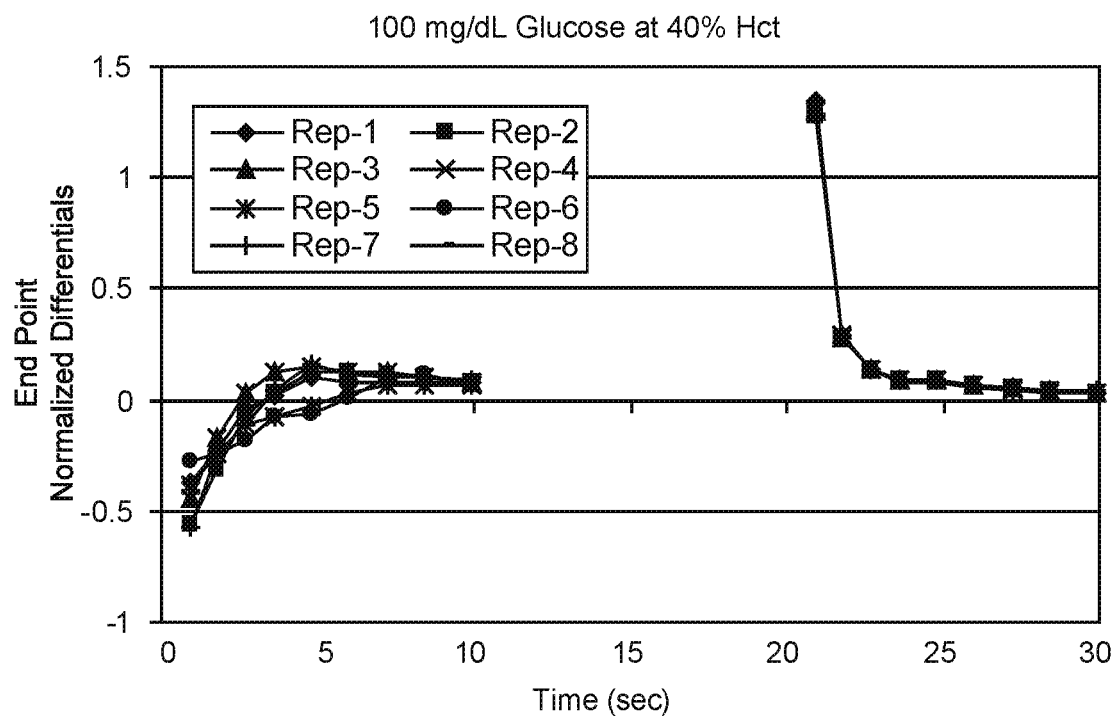
FIG. 4C plots the differentials of each output signal segment normalized by the end-point value of the second excitation.

The output signal segments were then processed to provide SSP parameters. The normalized differential method was used to process the output signal segments into SSP parameters by obtaining the differential between the first and the last data point (current value) for each segment, followed by normalization with the end-point reading of the continuous output signal measured at 29.9 seconds. FIG. 4C plots the differentials of each output signal segment normalized by the end-point reading of the second excitation. For example, the "9.9" segment was determined with $(i_{9sec} - i_{9.9sec})/i_{29.9sec}$ and the "20.9" segment was determined with $(i_{20.3sec} - i_{20.9sec})/i_{29.9sec}$.

Figure 4D:
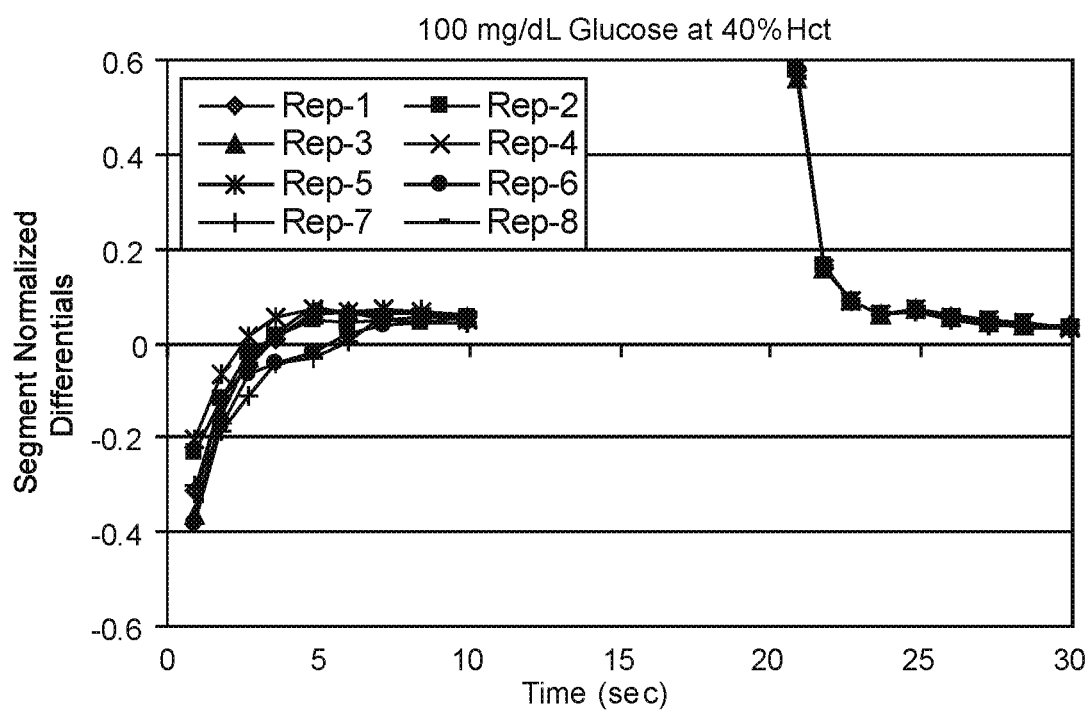
FIG. 4D plots the differentials of each output signal segment normalized by the end-point value of the excitation from which the segment values were recorded.

FIG. 4D plots the differentials of each output signal segment normalized by the end-point reading of the excitation from which the segment values were recorded. For example, using segment normalized differentials, the "$9.9_{snd}$" segment=$(i_{9sec} - i_{9.9sec})/i_{9.9sec}$, where the 9.9 second current value is the last current value recorded from the first input excitation, and the "$20.9_{snd}$" segment=$(i_{20.3sec} - i_{20.9sec})/i_{29.9sec}$, where the 29.9 second current value is the last current value recorded from the second input excitation.

Figure 4E:
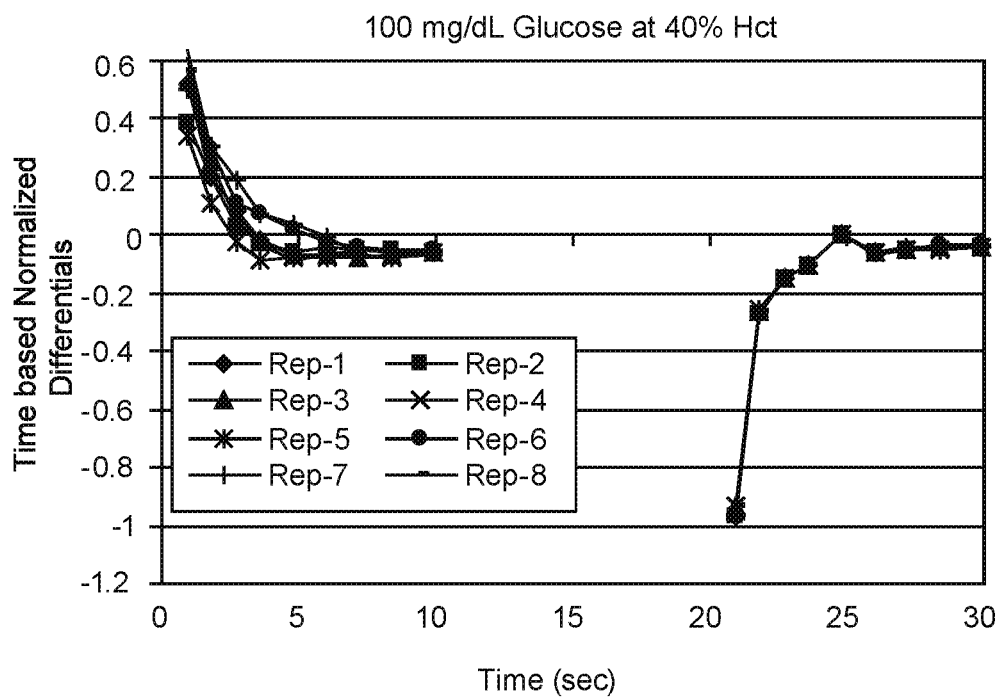
FIG. 4E plots the time-based differentials of each output signal segment normalized by the end-point value of the excitation from which the segment values were recorded.

FIG. 4E plots the time-based differentials of each output signal segment normalized by the end-point reading of the excitation from which the segment values were recorded. For instance, the time-based normalized differential may be represented by "$9.9_{tnd}$"=$(i_{9sec} - i_{9.9sec})/(9 \text{ s} - 9.9 \text{ s})/i_{9.9sec}$ and "$20.9_{tnd}$"=$(i_{20.3sec} - i_{20.9sec})/(20.3 \text{ s} - 20.9 \text{ s})/i_{29.9sec}$. These are time gradients (currents divided by time) within each segment with normalization by the segment end-point reading. Other methods may be used to process the output signal segments.

Once processed into SSP parameters, multiple SSP parameters, error parameters, and values representing the uncompensated analyte concentration of the sample may be considered as terms for potential inclusion in the complex index function, which served as the SSP function. Table 4, below, lists the weighing coefficients selected in view of the exclusion test/s from a multi-variable regression of SSP parameters, error parameters, and the uncompensated glucose concentration determined from end-point current 2 of the second excitation, as represented in FIG. 4A. MINITAB version 14 software was used with the Multi-Variant Regression of Linear Combinations of Multiple Variables option chosen to perform the multi-variable regression. Other statistical analysis or regression options may be used to determine the weighing coefficients for the terms.

TABLE 4

Results of two excitation multivariable regression.

| Terms | Weighing Coefficients |
|---|---|
| 6 | 0.64347 |
| 8.4 | 0.9601 |
| 20.9 | 42.281 |
| 21.8 | -170.670 |
| 23.6 | -8.0624 |
| 28.4 | 80.595 |
| G | 0.0028633 |
| R2/1 | 12.143 |
| R2 | 8.825 |
| 0.9*G | -0.0009523 |
| 20.9*G | 0.016148 |
| 21.8*G | -0.067240 |
| 27.2*G | -0.039550 |
| R2/1*G | -0.0043275 |
| 20.9*R2/1 | -64.138 |
| 21.8*R2/1 | 271.09 |
| 28.4*R2/1 | -116.44 |

The resulting complex index function which served as the SSP function may be represented as follows:

SSP Function=−12.384+0.64347*'6'+0.9601*'8.4'+ 42.281*'10.8'−170.67*'11.7'−8.0624*'13.5'+ 80.595*'18.3'+0.002863*'$G$'+12.143*'$R2/1$'+ 8.825*'$R2$'−0.0009523*'0.9*$G$'+ 0.016148*'20.9*$G$'−0.06724*'21.8*$G$'− 0.03955*'28.2*$G$'−0.0043275*'$R2/1$*$G$'− 64.138*'20.9*$R2/1$'+271.09*'21.8*$R2/1$'− 116.44*'28.4*$R2/1$' where G is the uncompensated glucose concentration of the sample, R2/1 is the end-point reading of the output from the second excitation over the end-point reading of the output from the first excitation, and R2 is the end-point reading of the output from the second excitation over the initial reading of the output from the second excitation. The SSP function will generate a value from all parameters within the function, which represents the system total error in the form of $\Delta S/S$. Thus, $G_{comp}=(i_{raw}-\text{Int})/[(S_{cal}*(1+\text{SSP}))]$ as the hematocrit compensated glucose value, where $i_{raw}$ is the output signal value used to determine the analyte concentration of the sample and Int may be 0.

Figure 4F:
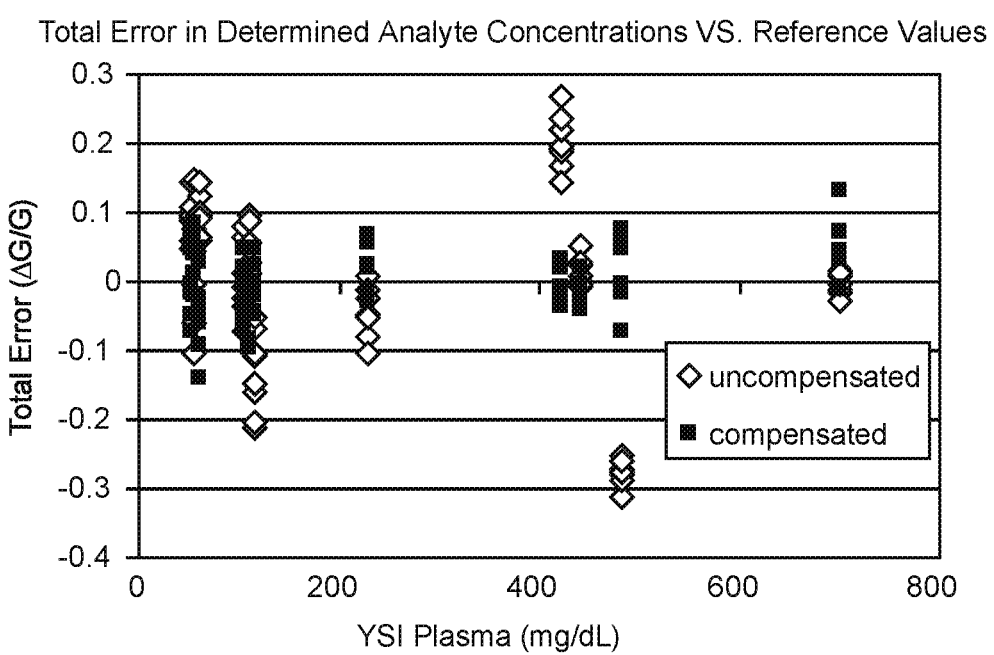
FIG. 4F compares the total relative error ($\Delta G/G$) of the uncompensated and SSP function compensated analyte concentrations determined from multiple blood samples including from 20% to 60% (volume/volume) hematocrit and glucose concentrations from approximately 50 to 700 mg/dL at approximately 25° C.

FIG. 4F compares the total relative error ($\Delta G/G$) of the uncompensated and SSP function compensated analyte concentrations determined from multiple blood samples including from 20% to 60% (volume/volume) hematocrit and glucose concentrations from approximately 50 to 700 mg/dL at approximately 25° C. As shown in the figure, a reduction in relative error of approximately 50% was provided when the SSP function provided primary compensation. Preferably, the SSP function provides a determined analyte concentration with 30% less, more preferably 40% less, and even more preferably 50% less, relative error than the uncompensated analyte compensation determined from the output signal and the conversion function.

FIG. 5A depicts the input signals applied to the test sensor for an electrochemical gated amperometric analysis where six relatively short excitations are separated by five relaxations of varying duration. In addition to the six excitations applied to the working and counter electrodes, a second input signal is applied to an additional electrode to generate a secondary output signal. The input signal was applied to the additional electrode after completion of the analytic input signal applied between the working and counter electrodes, but may be applied at other times. The input signal applied to the additional electrode included a seventh higher voltage pulse. The solid lines describe the substantially constant input potentials, while the superimposed dots indicate times of taking current measurements. This input signal was applied to multiple test sensors used to determine the glucose concentration of blood from multiple internal clinical studies. Such an analysis may be performed on a blood sample using a measurement device and a test sensor.

The excitations of the analytic input signal of FIG. 5A included pulse-widths of about 0.2, about 0.4, and about 0.5 seconds. While other pulse-widths may be used, pulse widths from about 0.1 to about 0.5 seconds are preferred. Pulse-widths greater than 2 seconds are less preferred. The analytic excitations are separated by relaxations of about 0.5 and about 1 second and were provided by open circuits. While other relaxation-widths may be used, relaxation-widths from about 0.3 to about 1.5 seconds are preferred. The relaxation-width directly preceding the excitation including the current measurement from which the concentration of the analyte is determined is preferably less than 1.5 second. Relaxation-widths greater than 5 seconds are less preferred. In addition to open circuits, relaxations may be provided by other methods that do not apply a potential that appreciably causes the analyte and/or mediator to undergo an electrochemical redox reaction. Preferably, the application of the analytic input signal and the measurement of the associated output currents from the sample are complete in seven seconds or less.

A secondary output signal in the form of a current from an additional electrode may be considered an error parameter describing the hematocrit content of a blood sample. The hematocrit content of the sample may be considered an error parameter because an error in concentration values may arise from performing an analysis at a hematocrit content other than that at which the reference correlation was determined. The hematocrit content of the sample may be determined from any source, such as an electrode, calculated estimates, and the like.

FIG. 5B depicts the output current values recorded from the six amperometric excitations and the secondary output signal. SSP parameters were determined from these output signals by normalizing the differential of each segmented signal by the current $i_{5,4}$, which is used to represent the end-point reading of the analysis. The $i_{5,4}$ current was used to represent the end-point reading, as of the multiple current values recorded, this current reading best described the analyte concentration of the sample. While another value could be selected as the end-point reading for normalization, preferably the end-point reading used for normalization is that which correlates best with the underlying analyte concentration of the sample.

The output currents from the individual excitations were segmented and converted to SSP parameters as follows: $d12=(i_{1,1}-i_{1,2})/i_{5,4}$, $d13=(i_{1,2}-i_{1,3})/i_{5,4}$, $d14=(i_{1,3}-i_{1,4})/i_{5,4}$, $d15=(i_{1,4}-i_{1,5})/i_{5,4}$, . . . . The output currents from the secondary output signal were normalized by $i_{7,4}$. The SSP parameters determined from FIG. 5B were d12, d13, d14, d15, d22, d32, d33, d34, d42, d43, d44, d52, d53, d54, d62, d63, d64, d72, d73, d74. Other SSP parameters may be used.

The remaining residual error (RRE) present after compensation by the primary and first residual functions may be generally represented by: $dG/G\_1=(G_{comp}1-G_{ref})/G_{ref}$. Once processed into SSP parameters, the multiple SSP parameters, cross-terms of the SSP parameters, and values representing the uncompensated analyte concentration of the sample may be considered as terms for potential inclusion in the complex index function, which served as the SSP function. Table 5, below, lists the weighing coefficients selected in view of the exclusion test/s resulting from a multi-variable regression. MINITAB version 14 software was used with the Multi-Variant Regression of Linear Combinations of Multiple Variables option chosen to perform the multi-variable regression. Other statistical analysis or regression options may be used to determine the weighing coefficients for the terms.

TABLE 5

Results of multi-excitation multivariable regression.

| Terms | Weighing Coefficients |
|---|---|
| Temp | 0.011077 |
| d12 | 0.11892 |
| d22 | −0.19642 |
| d33 | −14.314 |
| d34 | 18.401 |
| d42 | 0.30470 |
| d63 | 4.8410 |
| d73 | 2.5512 |
| d15G | −0.0021700 |
| d64G | −0.0068789 |
| d72G | 0.009718 |
| 7d13 | −0.00030004 |
| 7d33 | 0.0074282 |
| 7d34 | −0.009218 |
| 7d53 | −0.0018402 |
| d22d54G | 0.049078 |
| d62d72G | −0.014893 |
| 7d22G | −0.00000218 |

The resulting complex index function which served as the SSP function may be represented as follows:

SSP Function=−0.3161 9−0.011077*'T'+
0.1189*'d12'−0.1 964*'d22'−14.31*'d33'+
18.4*'d34'+0.3047*'d42'+4.841*'d63'+
2.551*'d73'−0.00217*'D15G'−
0.006879*'d64G'+0.009718*'d72G'−
0.0003*'7d13'+0.007428*'7d33'−
0.009218*'7d34'−0.00184*'7d53'+
0.04908*'d22d54G'−0.01489*'d62d72G'−
2.18e−6*'7d22G' where G is the uncompensated glucose concentration of the sample, T is temperature, 7d13 is an example of a cross-term formed by the end-point reading of seventh pulse times d13, and d22d54G is an example of a cross-term formed by multiplying d22, d54, and G.

Analyses were performed using four different manufacturing lots of test sensors to perform approximately 158 analyses. Approximately 79 of these analyses were from HCP-testing while the remaining approximately 79 analyses arose from user self-testing. Biosensor test sensors vary from lot-to-lot in their ability to reproducibly produce the same output signal in response the same input signal and sample analyte concentration. While preferable to equip the measurement device with a single reference correlation for the conversion function, doing so limits the manufacturing variance that can occur between different lots of test sensors.

Figure 6A:
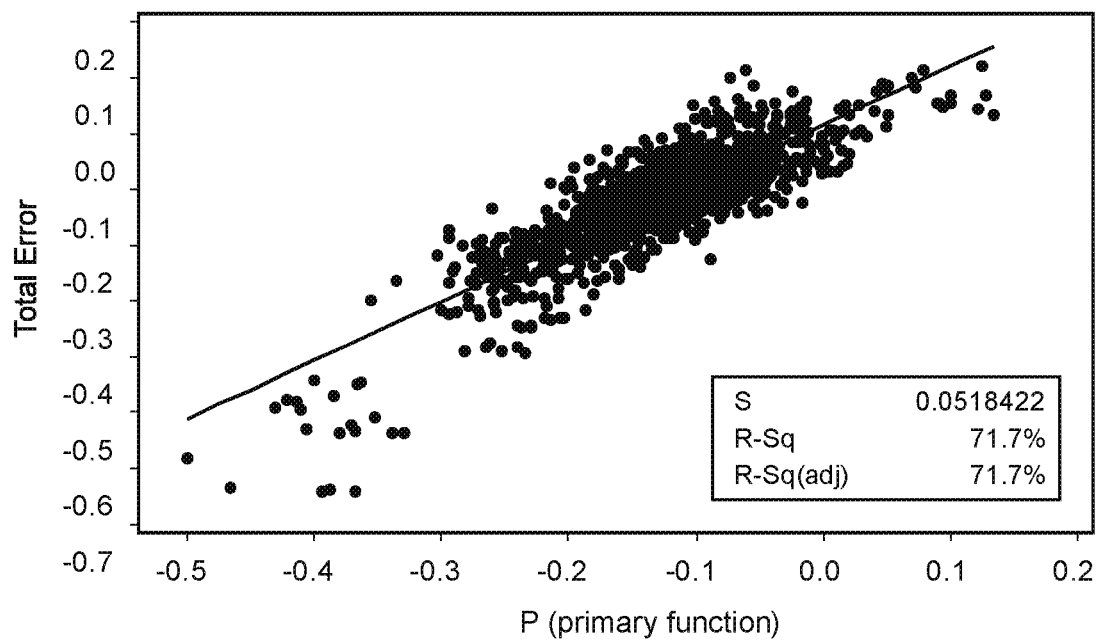
FIG. 6A is a correlation plot comparing the total error to the predicted error of the analyte concentrations determined using only the primary function.
Figure 6B:
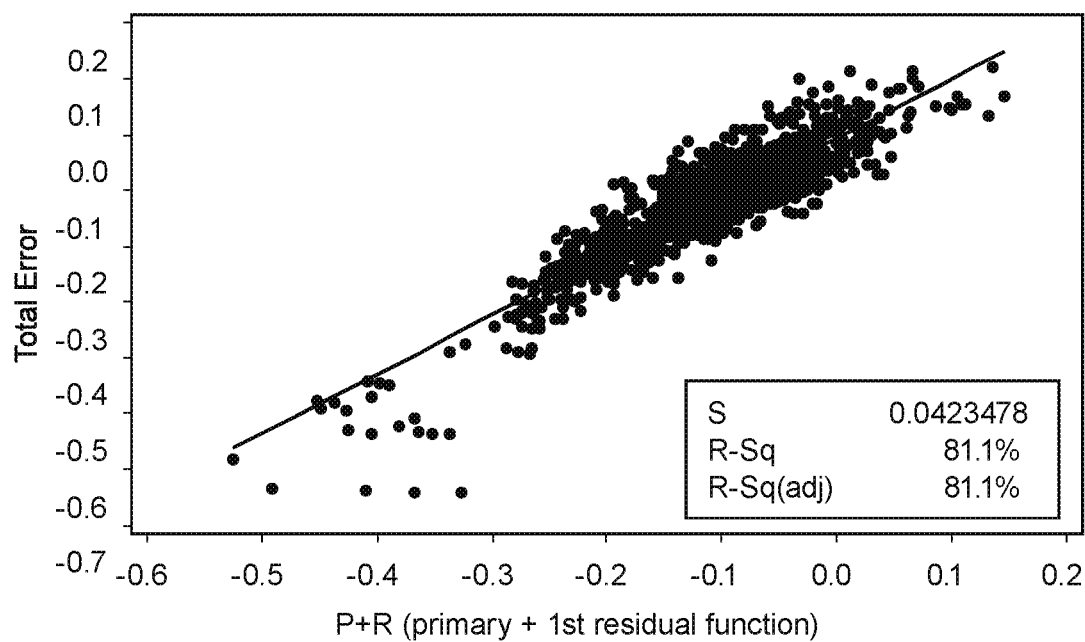
FIG. 6B is a correlation plot comparing the total error to the predicted error of the analyte concentrations determined using the primary and first residual function.
Figure 6C:
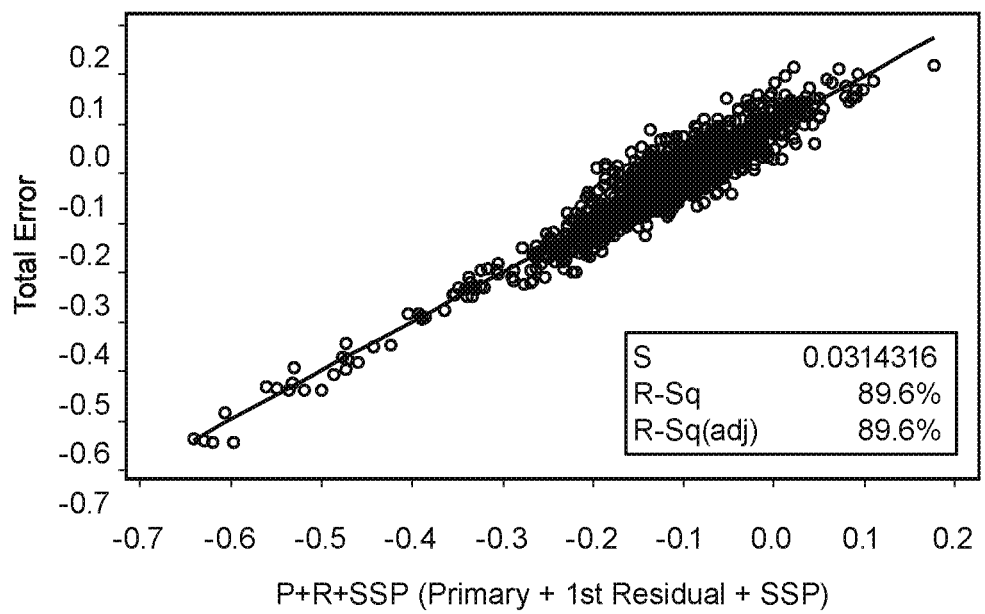
FIG. 6C is a correlation plot comparing the total error to the predicted error of the analyte concentrations determined using the primary function, first residual function, and SSP function.

FIG. 6A is a correlation plot comparing the total error to the predicted error of the analyte concentrations determined using only the primary function. FIG. 6B is a correlation plot comparing the total error to the predicted error of the analyte concentrations determined using the primary and first residual functions. FIG. 6C is a correlation plot comparing the total error to the predicted error of the analyte concentrations determined using the primary, first residual, and SSP functions.

Progressive improvements in measurement performance were observed from the first residual function and the SSP function in relation to primary function compensation alone. This was especially the case for the scattered data points. The improvement can be seen in the progressive reduction of the percent bias standard deviation term S (SD value, 0.0518, 0.0423, 0.0314) with respect to the regression line of the total error (dG/G), or the increase of the correlation coefficient $R^2$ values (71.7%, 81.1% and 89.6%).

Figure 6D:
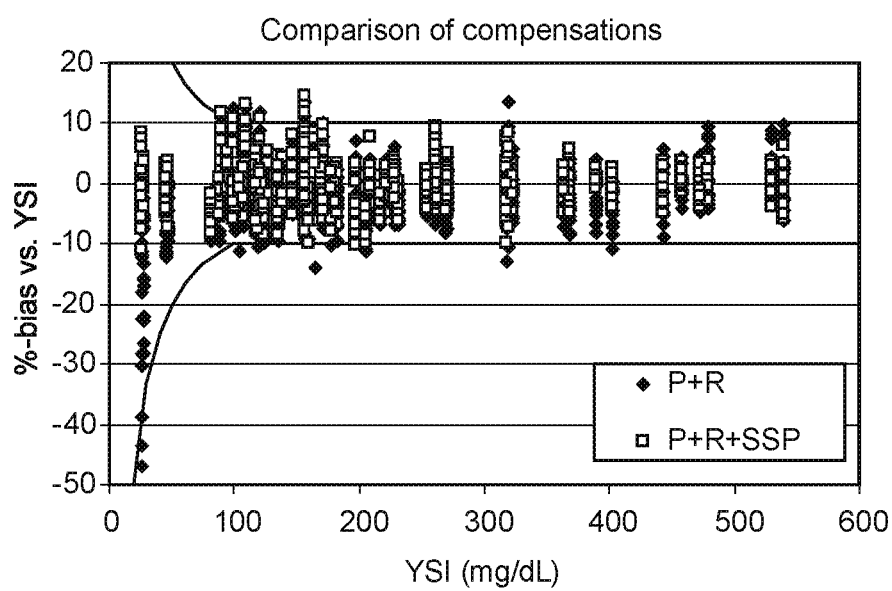
FIG. 6D and FIG. 6E compare the compensation results from primary+first residual and additional compensation with the SSP function.
Figure 6E:
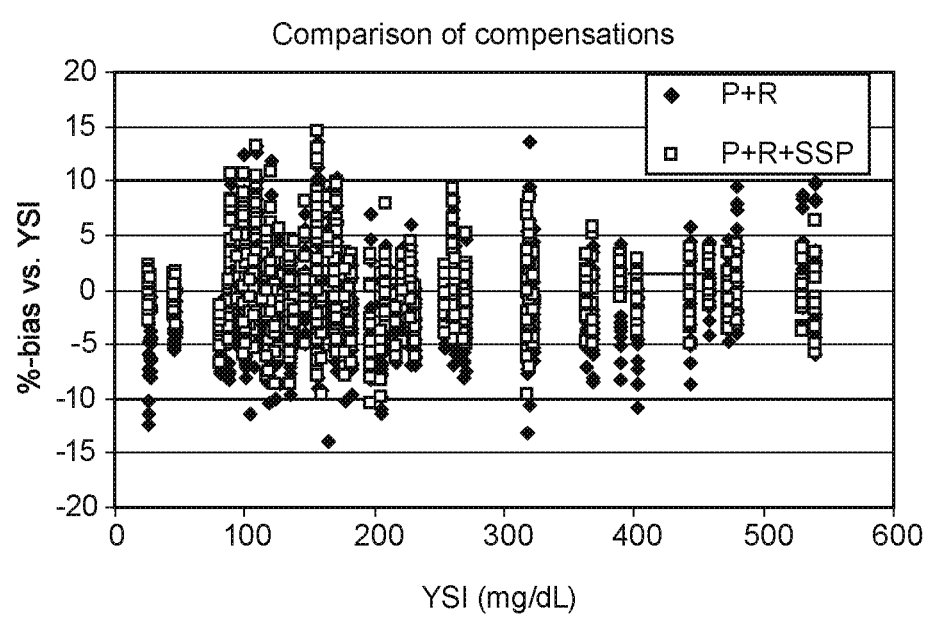

Thus, the compensated analyte concentration may be generally determined with the relationship (concentration determined from primary and first residual compensation)/(1+SSP function). FIG. 6D and FIG. 6E compare the compensation results from primary+first residual and additional compensation with the SSP function. In FIG. 6D, the %-bias is expressed in pure percent, that is, %-bias=100%×($G_{final}$−$G_{ref}$)/$G_{ref}$ with expanded boundary±100%×(10/Gref) after 100 mg/dL. In FIG. 6E, the %-bias is expressed pure percent for G≥2100 mg/dL, and bias ($G_{final}$−$G_{ref}$) for G<100 mg/dL with fixed boundary of ±10%. These two expressions are equivalent, but FIG. 6D more readily shows the improvement in measurement performance in the low glucose region with the addition of SSP function compensation.

Figure 7A:
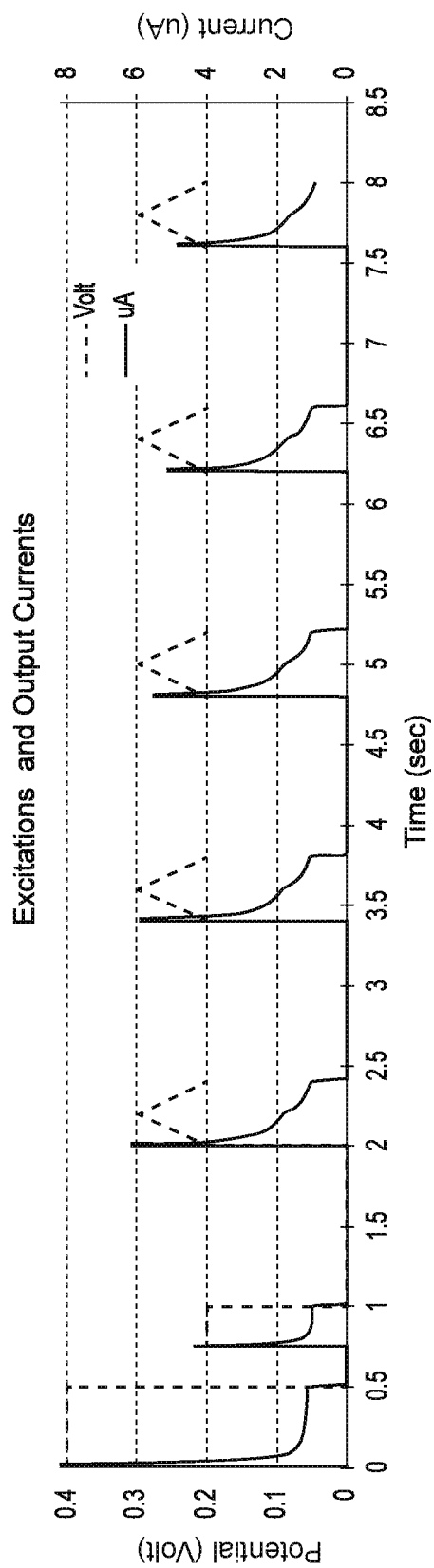
FIG. 7A represents the input signals applied to the working and counter electrodes of a test sensor for an electrochemical combined gated amperometric and gated voltammetric analysis.

FIG. 7A represents the input signal applied to the working and counter electrodes of a test sensor for an electrochemical combined gated amperometric and gated voltammetric analysis. The input signal included two amperometric excitations followed by five voltammetric excitations. The excitations were separated by six relaxations of varying duration. The dashed lines represent the input signal and show that the amperometric excitations were applied at a substantially constant voltage/potential, while the voltammetric excitations are triangular in shape, thus having a potential that changes with time. In this example, the voltage scan rate was 0.5 V/second for the voltammetric excitations, although other scan rates may be used. The output currents measured from the sample for each excitation in micro amps (uA) are represented by the corresponding solid lines. Output current values were recorded about every 10 milliseconds for each voltammetric excitation. While the amperometric excitations produced a continuous decay, the voltammetric excitations provided a two-step decay with respect to time from the forward and reverse portion of each voltammetric excitation. Such an analysis may be performed on a blood sample using a measurement device and a test sensor.

The amperometric excitations of the input signal of FIG. 7A have pulse-widths of about 0.5 and 0.25 seconds. The voltammetric excitations of the analytic input signal included pulse-widths of about 0.4 seconds. While other pulse-widths may be used, pulse widths from about 0.1 to about 0.5 seconds are preferred. Pulse-widths greater than 2 seconds are less preferred. Preferably, the scan range of the voltammetric excitation from which the analyte concentration of the sample is determined is within the plateau range of the measurable species so that the electrochemical redox reaction of the measurable species is substantially diffusion limited.

The voltammetric analytic excitations were separated by relaxations of about 1 second and were provided by open circuits. While other relaxation-widths may be used, relaxation-widths from about 0.3 to about 1.5 seconds are preferred. The relaxation-width directly preceding the excitation including the current measurement from which the concentration of the analyte was determined is preferably less than 1.5 second. Relaxation-widths greater than 3 seconds are less preferred. In addition to open circuits, relaxations may be provided by other methods that do not apply a potential that appreciably causes the analyte and/or mediator to undergo an electrochemical redox reaction during the relaxation. Preferably, the application of the analytic input signal and the measurement of the associated output currents from the sample are complete in eight seconds or less.

Figure 7B:
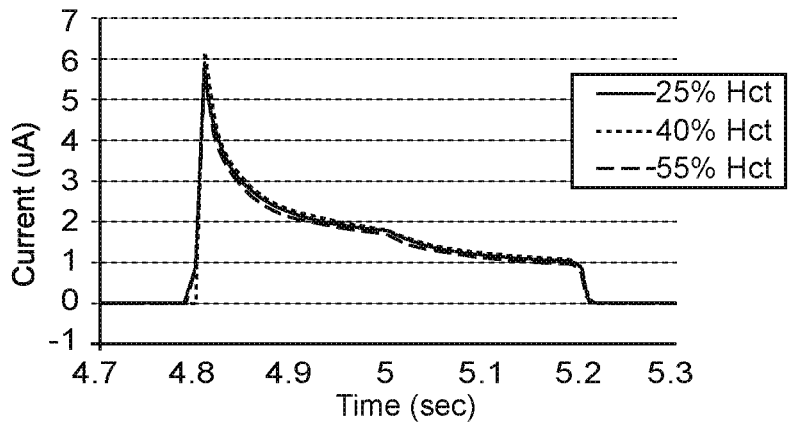
FIG. 7B shows the currents obtained for multiple analyses from the third voltammetric excitation of a seven excitation input signal having two amperometric and five voltammetric excitations.

FIG. 7B shows the currents obtained for multiple analyses from the third voltammetric excitation of the seven excitation input signal having two amperometric and five voltammetric excitations. The analyses were performed on blood samples including about 80 mg/dL of glucose as the analyte and 25%, 40%, or 55% hematocrit by volume. Table 6, below shows the time from the application of the input signal to the sample and the time within the pulse for the output signal current value recorded from the third voltammetric excitation.

TABLE 6

| Output signal measured current values | | |
|---|---|---|
| Time from input signal application, sec. | Time within pulse, sec. | Measured Current, uA. |
| 4.81 | 0.01 | 10.05638 |
| 4.86 | 0.06 | 5.94202 |
| 4.91 | 0.11 | 4.706399 |
| 5 | 0.2 | 3.766113 |
| 5.01 | 0.21 | 3.57111 |
| 5.11 | 0.31 | 2.729612 |
| 5.2 | 0.4 | 2.208661 |

Figure 7C:
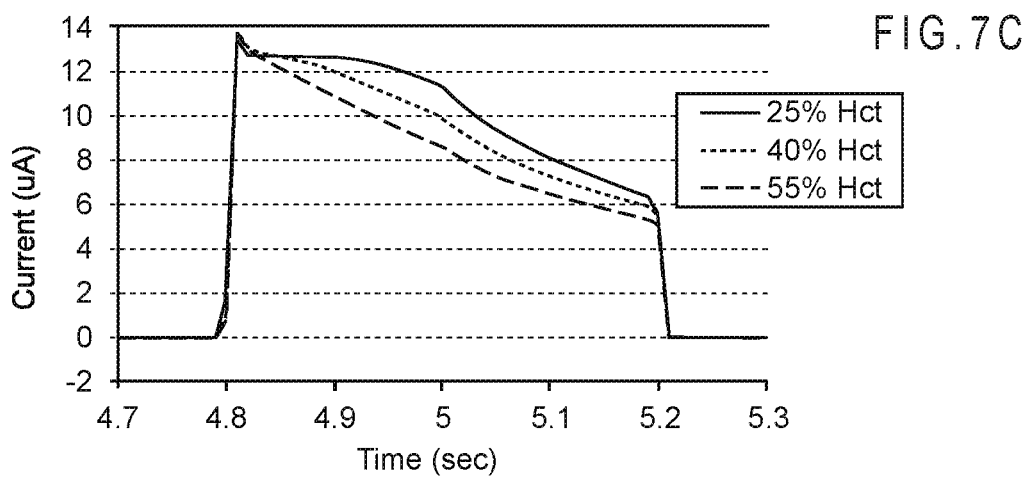
FIG. 7C shows the currents obtained from the third voltammetric excitation when the blood samples included about 400 mg/dL glucose.

FIG. 7C shows the currents obtained from the third voltammetric excitation when the blood samples included about 400 mg/dL glucose. As may be seen in the figure, the hematocrit content of the sample had a larger effect on the output currents for the higher glucose concentration blood samples.

Figure 7D:
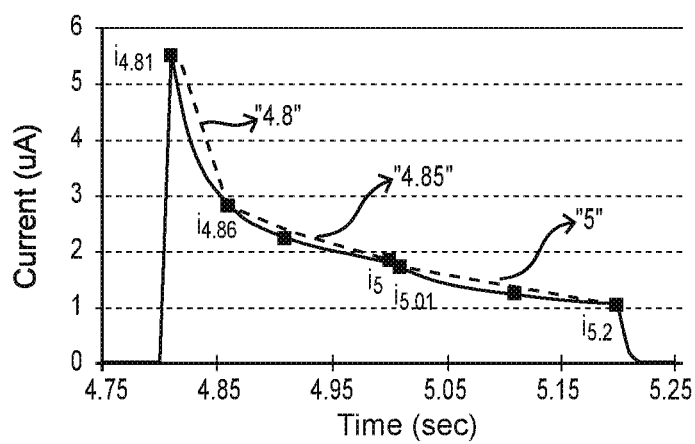
FIG. 7D represents how the output currents from the third voltammetric excitation were segmented to provide three output signal segments from the excitation.

FIG. 7D represents how the output currents from the third voltammetric excitation were segmented to provide three output signal segments "4.8", "4.85", and "5" from the excitation. The segments were labeled with the time after initiation of the input signal corresponding to the first current value of each segment.

In this example, the output currents from the five gated voltammetric excitations were segmented into two segments for the forward portion of the excitation and into one segment for the reverse portion of the excitation. Thus, three SSP parameters were determined from each gated voltammetric excitation. Additional SSP parameters may be calculated from one or more of the excitations for either the forward or reverse portions of the excitation.

SSP parameters were then determined from the output currents from the third voltammetric excitation. While other SSP parameter determining methods may be used, each of the previously described methods were used to provide three SSP parameters "4.8", "4.85", and "5" for the third voltammetric excitation as in Table 7, below.

TABLE 7

SSP Parameter Determination

| SSP Par. | Avg | Ratio | Diff | Nml Diff | TD | TnD | Decay K | Decay R |
|---|---|---|---|---|---|---|---|---|
| '4.8' | 7.9992 | 0.5908 | 4.114 | 1.862 | 82.287 | 37.256 | 0.293 | 0.006 |
| '4.85' | 4.8540 | 0.6338 | 2.175 | 0.985 | 43.518 | 7.036 | 0.378 | 0.039 |
| '5' | 2.8898 | 0.6184 | 1.362 | 0.616 | 15.138 | 3.246 | 0.745 | 0.212 |

To perform the compensation, SSP parameters were determined from the segments from the remaining voltammetric excitations using the time-based normalized differential SSP parameter generation method by normalizing the differential of each segmented signal by the current $i_{5.2}$, which represented the end-point reading of the third excitation and was measured at 5.2 seconds after the initiation of the application of the input signal to the sample. For this gated input signal, the output signals from each excitation were normalized with the end-point reading of the excitation. Thus, three SSP parameters were determined from each of the five voltammetric excitations represented in FIG. 7A. If the analysis end-point, as opposed to each intermediate end-point from the excitations had been used to determine the SSP parameters, is would have been the normalization value.

Thus, the time-based normalized differential SSP parameter generation method was used, $[\Delta i/(-\Delta t)/i_{EP}]$, where the $i_{EP}$ value used for normalization was the end-point current of each excitation. The output currents from the individual voltammetric excitations were segmented and converted to SSP parameters as follows: $4.8=(i_{4.81}-i_{4.86})/(4.86-4.81)/i_{5.2}$, $4.85=(i_{4.86}-i_5)/(5-4.86)/i_{5.2}$, and $5=(i_{5.01}-i_{5.2})/(5.2-5.01)/i_{5.2}$, as an example. This general method was applied to the output currents from the five voltammetric excitations of FIG. 7A to produce the SSP parameters as in Table 8, below.

TABLE 8

SSP Parameters from Gated Voltammetric Excitations

| Voltammetric Excitation | SSP Parameters |
|---|---|
| 3 | "2.0" = $(i_{2.01} - i_{2.06})/(2.06 - 2.01)/i_{2.4}$ |
|  | "2.05" = $(i_{2.06} - i_{2.2})/(2.2 - 2.06)/i_{2.4}$ |
|  | "2.2" = $(i_{2.21} - i_{2.4})/(2.4 - 2.21)/i_{2.4}$ |
| 4 | "3.4" = $(i_{3.41} - i_{3.46})/(3.46 - 3.41)/i_{3.8}$ |
|  | "3.45" = $(i_{3.46} - i_{3.6})/(3.6 - 3.46)/i_{3.8}$ |
|  | "3.6" = $(i_{3.61} - i_{3.8})/(3.8 - 3.61)/i_{3.8}$ |
| 5 | "4.8" = $(i_{4.81} - i_{4.86})/(4.86 - 4.81)/i_{5.2}$ |
|  | "4.85" = $(i_{4.86} - i_5)/(5 - 4.86)/i_{5.2}$ |
|  | "5" = $(i_{5.01} - i_{5.2})/(5.2 - 5.01)/i_{5.2}$ |
| 6 | "6.2" = $(i_{6.21} - i_{6.26})/(6.26 - 6.21)/i_{6.6}$ |
|  | "6.25" = $(i_{6.26} - i_{6.4})/(6.4 - 6.26)/i_{6.6}$ |
|  | "6.4" = $(i_{6.41} - i_{6.6})/(6.6 - 6.41)/i_{6.6}$ |
| 7 | "7.6" = $(i_{7.61} - i_{7.66})/(7.66 - 7.61)/i_8$ |
|  | "7.65" = $(i_{7.66} - i_{7.8})/(7.8 - 7.626)/i_8$ |
|  | "7.8" = $(i_{7.81} - i_8)/(8 - 7.81)/i_8$ |

A complex index function determined from these SSP parameters to provide a SSP function may be represented as follows:

SSP Function=−1.4137−0.0059269*'2.0'−
0.38649*'2.05'+1.605*'2.2'−2.3567*'3.6'+
2.1962*'4.85'−1.9223*'6.25'+0.87157*'6.4'+
0.27137*'7.65'−0.00021187*'2G'−
0.0039181*'2.2G'+0.00026258*'3.4G'+
0.0064633*'3.45G'+0.0037505*'3.6G'−
0.014191*'4.85G'+0.0078856*'6.25G' where G is the uncompensated glucose concentration of the sample and "2.0"*G is an example of a cross-term formed by the product of the "2.0" SSP parameter and the uncompensated glucose concentration of the sample.

The uncompensated glucose concentration of the sample was determined with the general relationship $G=(i_{5.2}-\text{Int})/S_{cal}$, where $i_{5.2}$ is the current value measured after 5.2 seconds of initiating the input signal from the third gated voltammetric excitation, Int is the intercept of a reference correlation, which may be 0, and $S_{cal}$ is the reference correlation relating output currents from the measurement device to known sample analyte concentrations as determined with a reference instrument. In this example, the end-point current of the third voltammetric excitation was used to determine the analyte concentration of the sample; however, an intermediate current from within an excitation also may be used to determine the analyte concentration of the sample. Table 9 below shows how a sample analyte concentration was determined from both an intermediate current at 5.0 seconds and from the 5.2 second end-point current of the third voltammetric excitation. The slopes and intercepts in Table 9 were predetermined from regressions of multiple current readings at multiple glucose levels.

TABLE 9

Intermediate and End-Point Current Concentrations

| YSI, mg/dL | i_5.0, uA | i_5.2, uA | G_5.0, mg/dL | G_5.2, mg/dL | % bias_5.0 | % bias_5.2 |
|---|---|---|---|---|---|---|
| 79.2 | 1.71 | 1.14 | 83.81 | 80.01 | 5.8 | 1.0 |
| 170.5 | 3.61 | 2.61 | 170.29 | 172.18 | −0.1 | 1.0 |
| 278.5 | 5.88 | 4.34 | 273.66 | 280.25 | −1.7 | 0.6 |
| 452.0 | 9.90 | 7.12 | 457.29 | 455.06 | 1.2 | 0.7 |
| Slope$_{RC}$ | 0.0219 | 0.0159 | | | | |
| Intercept$_{RC}$ | −0.1279 | −0.1333 | | | | |

The reference analyte concentrations for the samples were determined with a YSI reference instrument. The slope and intercept values for the reference correlation were previously determined for a blood sample including a known glucoses concentration of 175 mg/dL and a hematocrit content of 40%. The output current values recorded for the samples at 5.0 seconds and at 5.2 seconds were used with the reference correlation to determine the sample analyte concentrations. The percent biases for the determined analyte concentrations were determined in relation to the reference analyte concentrations.

While compensation may be used in addition to the SSP function for gated voltammetric input signals, in this example the SSP function was used to provide primary compensation generally in accord with FIG. 2B using the general relationship $G_{comp}=G/(1+\text{SSP Function})$, where $G_{comp}$ is the SSP parameter compensated analyte concentration of the sample. Either the G_5.0 or the G_5.2 determined analyte concentrations from Table 7 may be compensated in this way. The previously discussed SSP compensation methods also may be used with analyte concentrations determined in these ways.

Figure 7E:
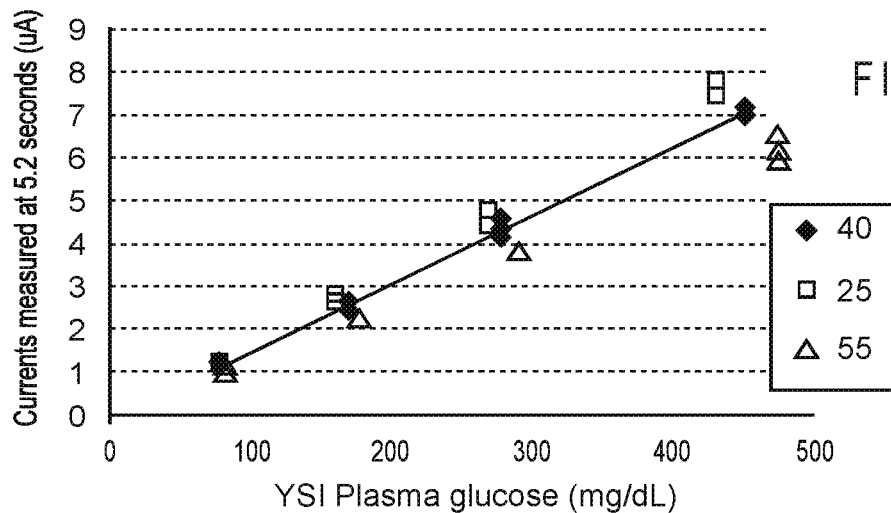
FIG. 7E shows the currents measured at 5.2 seconds from the third gated voltammetric excitation for blood samples including about 80 mg/dL, 170 mg/dL, 275 mg/dL, or 450 mg/dL glucose with hematocrit levels of 25%, 40%, or 55% by volume.

FIG. 7E shows the currents measured at 5.2 seconds from the third gated voltammetric excitation for blood samples including about 80 mg/dL, 170 mg/dL, 275 mg/dL, or 450 mg/dL glucose with hematocrit levels of 25%, 40%, or 55% by volume. As can be seen from the graph, there is greater divergence from the 40% Hct line by the 25% and 55% Hct samples at higher glucose concentrations. The reference glucose concentration of the samples was determined with a YSI reference instrument in the laboratory.

Figure 7F:
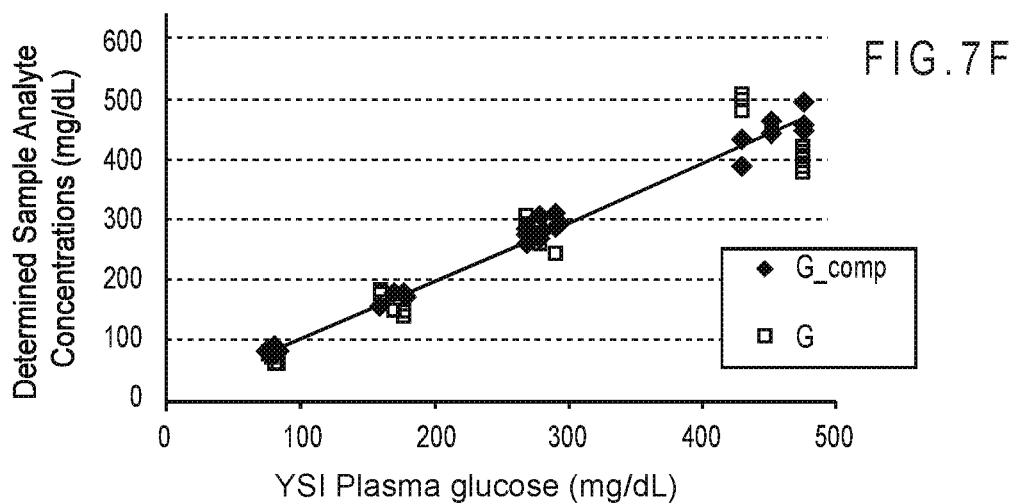
FIG. 7F shows the glucose readings obtained from the measurement device with and without compensation provided by the SSP function.

FIG. 7F shows the glucose readings obtained from the measurement device with and without compensation provided by the SSP function. The uncompensated analyte concentration (G) of each sample was determined with the general relationship $G=(i_{5.2}-\text{Int})/S_{cal}$, where Int and $S_{cal}$ are from a reference correlation determined in the laboratory with a YSI reference instrument from multiple analyses. The compensated analyte concentration (G_comp) of each sample was determined with the general relationship $G_{comp}=G/(1+\text{SSP Function})$. As seen in the figure, the compensated analyte concentrations are more closely grouped for the different analyte concentrations and Hct volumes.

Figure 7G:
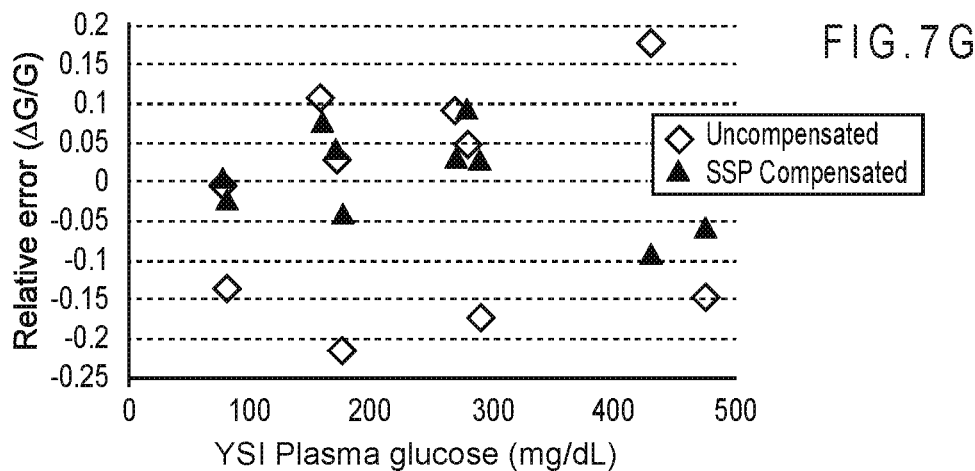
FIG. 7G compares the relative error between the determined SSP compensated and uncompensated glucose analyte concentrations for the blood samples.

FIG. 7G compares the relative error between the determined SSP compensated and uncompensated glucose analyte concentrations for the blood samples. Even at high glucose concentration, the SSP compensated determined analyte concentrations are close to the 0 error line, especially in comparison to the uncompensated determined analyte concentrations. The percent bias standard deviation for the uncompensated determined analyte concentrations was 13.5% while that for the SSP function compensated determined analyte concentrations was 5.9%. Thus, the SSP function compensation provided an approximately 56% (13.5−5.9/13.5*100) reduction in relative error in comparison to the analyte concentrations determined without SSP compensation.

Figure 8:
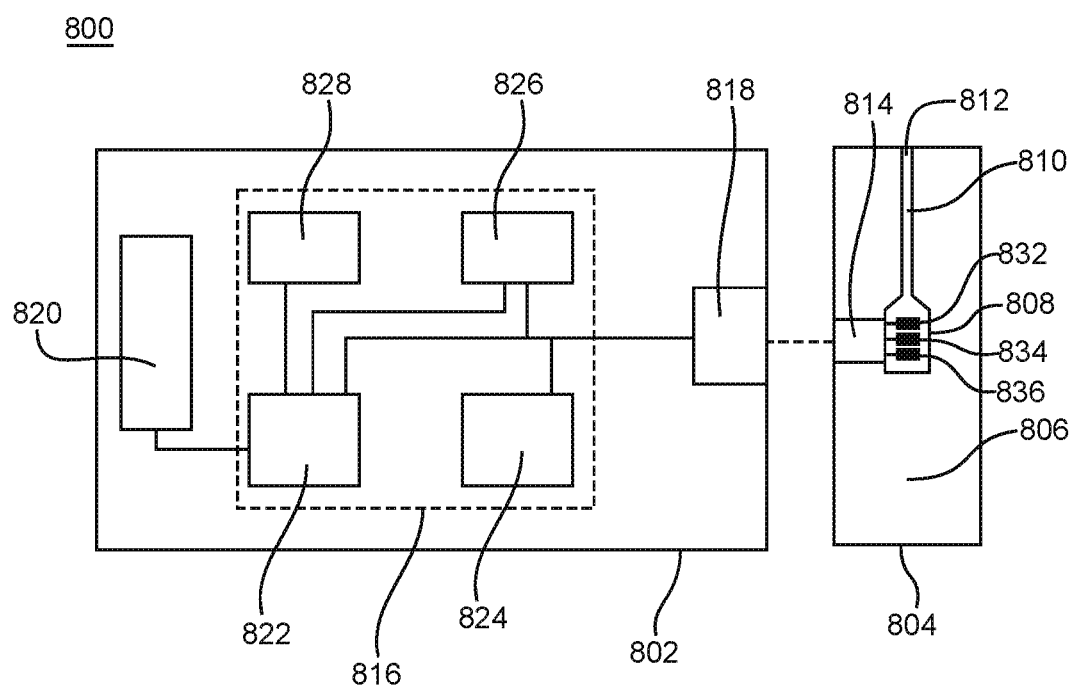
FIG. 8 depicts a schematic representation of a biosensor system that determines an analyte concentration in a sample of a biological fluid.

FIG. 8 depicts a schematic representation of a biosensor system 800 that determines an analyte concentration in a sample of a biological fluid. Biosensor system 800 includes a measurement device 802 and a test sensor 804. The measurement device 802 may be implemented in any analytical instrument, including a bench-top device, a portable or hand-held device, or the like. The measurement device 802 and the test sensor 804 may be adapted to implement an electrochemical sensor system, an optical sensor system, a combination thereof, or the like.

The biosensor system 800 determines the analyte concentration of the sample from a method of error compensation including at least one conversion function, at least one SSP function, and the output signal. The method of error compensation may improve the measurement performance of the biosensor system 800 in determining the analyte concentration of the sample. The biosensor system 800 may be utilized to determine analyte concentrations, including those of glucose, uric acid, lactate, cholesterol, bilirubin, and the like. While a particular configuration is shown, the biosensor system 800 may have other configurations, including those with additional components.

The test sensor 804 has a base 806 that forms a reservoir 808 and a channel 810 with an opening 812. The reservoir 808 and the channel 810 may be covered by a lid with a vent. The reservoir 808 defines a partially-enclosed volume. The reservoir 808 may contain a composition that assists in retaining a liquid sample such as water-swellable polymers or porous polymer matrices. Reagents may be deposited in the reservoir 808 and/or the channel 810. The reagents may include one or more enzymes, binders, mediators, and like species. The reagents may include a chemical indicator for an optical system. The test sensor 804 may have other configurations.

In an optical sensor system, the sample interface 814 has an optical portal or aperture for viewing the sample. The optical portal may be covered by an essentially transparent material. The sample interface 814 may have optical portals on opposite sides of the reservoir 808.

In an electrochemical system, the sample interface 814 has conductors connected to a working electrode 832 and a counter electrode 834 from which the analytic output signal may be measured. The sample interface 814 also may include conductors connected to one or more additional electrodes 836 from which secondary output signals may be measured. The electrodes may be substantially in the same plane or in more than one plane. The electrodes may be disposed on a surface of the base 806 that forms the reservoir 808. The electrodes may extend or project into the reservoir 808. A dielectric layer may partially cover the conductors and/or the electrodes. The sample interface 814 may have other electrodes and conductors.

The measurement device 802 includes electrical circuitry 816 connected to a sensor interface 818 and an optional display 820. The electrical circuitry 816 includes a processor 822 connected to a signal generator 824, an optional temperature sensor 826, and a storage medium 828.

The signal generator 824 provides an electrical input signal to the sensor interface 818 in response to the processor 822. In optical systems, the electrical input signal may be used to operate or control the detector and light source in the sensor interface 818. In electrochemical systems, the electrical input signal may be transmitted by the sensor interface 818 to the sample interface 814 to apply the electrical input signal to the sample of the biological fluid. The electrical input signal may be a potential or current and may be constant, variable, or a combination thereof, such as when an AC signal is applied with a DC signal offset. The electrical input signal may be applied continuously or as multiple excitations, sequences, or cycles. The signal generator 824 also may record an output signal from the sensor interface as a generator-recorder.

The optional temperature sensor 826 determines the temperature of the sample in the reservoir of the test sensor 804. The temperature of the sample may be measured, calculated from the output signal, or presumed to be the same or similar to a measurement of the ambient temperature or the temperature of a device implementing the biosensor system. The temperature may be measured using a thermister, thermometer, or other temperature sensing device. Other techniques may be used to determine the sample temperature.

The storage medium 828 may be a magnetic, optical, or semiconductor memory, another storage device, or the like. The storage medium 828 may be a fixed memory device, a removable memory device, such as a memory card, remotely accessed, or the like.

The processor 822 implements the analyte analysis and data treatment using computer readable software code and data stored in the storage medium 828. The processor 822 may start the analyte analysis in response to the presence of the test sensor 804 at the sensor interface 818, the application of a sample to the test sensor 804, in response to user input, or the like. The processor 822 directs the signal generator 824 to provide the electrical input signal to the sensor interface 818. The processor 822 receives the sample temperature from the temperature sensor 826. The processor 822 receives the output signal from the sensor interface 818. The output signal is generated in response to the reaction of the analyte in the sample. The output signal may be generated using an optical system, an electrochemical system, or the like. The processor 822 determines analyte concentrations from output signals using a compensation method including a conversion function and at least one SSP function as previously discussed. Once the desired segments are determined for the biosensor system, they may be implemented as the segmenting routine in the measurement device. The processor 822 selects which values of the output signal to process for two or more segments for SSP parameter processing based on a predetermined segmenting routine as stored in the storage medium 828. The results of the analyte analysis may be output to the display 820, a remote receiver (not shown), and/or may be stored in the storage medium 828.

The reference correlation between reference analyte concentrations and output signals from the measurement device 802 and other correlations, such as index functions, may be represented graphically, mathematically, a combination thereof, or the like. Correlation equations may be represented by a program number (PNA) table, another look-up table, or the like that is stored in the storage medium 828. Constants and weighing coefficients also may be stored in the storage medium 828.

Instructions regarding implementation of the analyte analysis also may be provided by the computer readable software code stored in the storage medium 828. The code may be object code or any other code describing or controlling the functionality described herein. The data from the analyte analysis may be subjected to one or more data treatments, including the determination of decay rates, K constants, ratios, functions, and the like in the processor 822.

In electrochemical systems, the sensor interface 818 has contacts that connect or electrically communicate with the conductors in the sample interface 814 of the test sensor 804. The sensor interface 818 transmits the electrical input signal from the signal generator 824 through the contacts to the connectors in the sample interface 814. The sensor interface 818 also transmits the output signal from the sample through the contacts to the processor 822 and/or signal generator 824.

In light-absorption and light-generated optical systems, the sensor interface 818 includes a detector that collects and measures light. The detector receives light from the liquid sensor through the optical portal in the sample interface 814. In a light-absorption optical system, the sensor interface 818 also includes a light source such as a laser, a light emitting diode, or the like. The incident beam may have a wavelength selected for absorption by the reaction product. The sensor interface 818 directs an incident beam from the light source through the optical portal in the sample interface 814. The detector may be positioned at an angle such as 45° to the optical portal to receive the light reflected back from the sample. The detector may be positioned adjacent to an optical portal on the other side of the sample from the light source to receive light transmitted through the sample. The detector may be positioned in another location to receive reflected and/or transmitted light.

The optional display 820 may be analog or digital. The display 820 may include a LCD, a LED, an OLED, a vacuum fluorescent, or other display adapted to show a numerical reading. Other display technologies may be used. The display 820 electrically communicates with the processor 822. The display 820 may be separate from the measurement device 802, such as when in wireless communication with the processor 822. Alternatively, the display 820 may be removed from the measurement device 802, such as when the measurement device 802 electrically communicates with a remote computing device, medication dosing pump, and the like.

In use, a liquid sample for analysis is transferred into the reservoir 808 by introducing the liquid to the opening 812. The liquid sample flows through the channel 810, filling the reservoir 808 while expelling the previously contained air. The liquid sample chemically reacts with the reagents deposited in the channel 810 and/or reservoir 808.

The test sensor 802 is disposed in relation to the measurement device 802, such that the sample interface 814 is in electrical and/or optical communication with the sensor interface 818. Electrical communication includes the transfer of input and/or output signals between contacts in the sensor interface 818 and conductors in the sample interface 814. Optical communication includes the transfer of light between an optical portal in the sample interface 814 and a detector in the sensor interface 818. Optical communication also includes the transfer of light between an optical portal in the sample interface 814 and a light source in the sensor interface 818.

The processor 822 directs the signal generator 824 to provide an input signal to the sensor interface 818. In an optical system, the sensor interface 818 operates the detector and light source in response to the input signal. In an electrochemical system, the sensor interface 818 provides the input signal to the sample through the sample interface 814. The processor 822 receives the output signal generated in response to the redox reaction of the analyte in the sample as previously discussed.

The processor 822 determines the analyte concentration of the sample from the output signals using a compensation system including a conversion function and at least one SSP function. The processor 822 also may implement primary and/or residual functions in the compensation system. Other compensations and functions also may be implemented by the processor 822.

While various embodiments of the invention have been described, it will be apparent to those of ordinary skill in the art that other embodiments and implementations are possible within the scope of the invention.

What is claimed is:

1. A method of operating a biosensor system, the method comprising:
   providing a biosensor system in the form of an analytical instrument including
      a measurement device having electrical circuitry communicatively coupled to a processor, a storage medium, a signal generator, and a sensor interface, the processor having instructions and data stored in the storage medium, and
      a test sensor having a base and a sample interface, the base forming a reservoir and a channel with an opening, the reservoir being in electrical or optical communication with the measurement device, the test sensor having a chemical reagent capable of reacting with an analyte in a biological fluid sample;
   receiving the biological fluid sample in the opening of the reservoir, the biological fluid sample flowing through the channel to fill at least in part the reservoir of the test sensor, the biological fluid sample including the analyte, the analyte in the biological fluid sample reacting in a chemical reaction with the chemical reagent in the reservoir;
   in response to the chemical reaction in the reservoir, generating an input signal from the signal generator for excitation of a chemical reaction product during an excitation period, the input signal including at least one excitation having a time period with an end-point;
   transmitting the input signal by the sensor interface to the sample interface for applying the input signal to the biological fluid sample;
   in response to the input signal and the concentration of the analyte in the biological fluid sample, generating, by the processor, one or more output signals from the test sensor;
   segmenting, by the processor, the one or more output signals during the excitation period into at least two segments with a regular or irregular segmenting interval, each segment including point readings obtained before the end-point of the input signal during the excitation period;
   converting, by the processor, the at least two segments into at least two signal processing parameters, wherein the signal processing parameters describe a portion of a total error in the one or more output signals;
   determining, by the processor, a segmented signal processing function from the signal processing parameters;
   using, by the processor, a predetermined reference correlation to relate the one or more output signals to a plurality of known sample analyte concentrations;
   in response to the predetermined reference correlation, using, by the processor, a conversion function to convert the one or more output signals into one known sample analyte concentration of the plurality of known sample analyte concentrations;
   determining, by the processor, a compensated value from the one or more output signals in response to the conversion function and the segmented signal processing function;
   determining, by the processor, the analyte concentration in the biological fluid sample from the compensated value of the one or more output signals; and
   outputting, by the processor, the analyte concentration to one or more of a display, a remote receiver, or a storage medium.

2. The method of claim 1, wherein the one or more output signals are responsive to a concentration of a measurable species in the biological fluid sample and the concentration of the measurable species in the biological fluid sample is responsive to the concentration of the analyte in the biological fluid sample.

3. The method of claim 2, wherein the concentration of the measurable species in the biological fluid sample is responsive to a chemical reaction between the analyte, an enzyme, and a mediator, where the chemical reaction is the redox reaction.

4. The method of claim 2, wherein the measurable species is light-identifiable.

5. The method of claim 1, further comprising continuously applying the input signal to the sample until an analysis end-point is reached.

6. The method of claim 5, further comprising measuring at least three output signal values from the one or more output signals.

7. The method of claim 1, wherein the input signal is gated and the excitation is applied until an intermediate analysis end-point is reached.

8. The method of claim 7, further comprising measuring at least two output signal values from the one or more output signals.

9. The method of claim 1, wherein the segmented signal processing function is predetermined.

10. The method of claim 9, wherein the at least two signal processing parameters are determined from the one or more output signals with a parameter determining method selected from the group consisting of averaging of signals within a segment, determining ratios of the signal values from within a segment, determining differentials of the signal values from within a segment, determining time-based differentials, determining normalized differentials, determining time-based normalized differentials, determining one or more decay constants, and determining one or more decay rates.

11. The method of claim 9, wherein the at least two signal processing parameters are determined using a parameter determining method selected from the group consisting of determining differentials of the signal values from within a segment, determining time-based differentials, determining normalized differentials, and determining time-based normalized differentials.

12. The method of claim 9, wherein the at least two signal processing parameters are determined using a parameter determining method selected from the group consisting of determining time-based differentials and determining time-based normalized differentials.

13. The method of claim 1, further comprising converting the one or more output signals with the conversion function before applying the segmented signal processing function.

14. The method of claim 1, wherein the analyte concentration in the biological fluid sample determined from the compensated value includes 30% less relative error than if the analyte concentration in the biological fluid sample were determined from the one or more output signals and the conversion function without the segmented signal processing function.

15. The method of claim 14, wherein the analyte concentration in the biological fluid sample determined from the compensated value includes 50% less relative error than if the analyte concentration in the biological fluid sample were determined from the one or more output signals and the conversion function without the segmented signal processing function.

16. The method of claim 13, wherein determining the compensated value from the one or more output signals in response to the conversion function and the segmented signal processing function further comprises determining the compensated value from the one or more output signals in response to a primary function, the segmented signal processing function not being the primary function, the primary function describing a major error in the one or more output signals and relating uncompensated output values and error contributors, the major error being attributable to one or more major error contributors selected from a group consisting of temperature, hematocrit, and hemoglobin.

17. The method of claim 16, wherein error described by the segmented signal processing function is substantially different than error described by the primary function.

18. The method of claim 16, further comprising modifying the segmented signal processing function and the primary function with function weighing coefficients.

19. A biosensor system for determining an analyte concentration in a biological fluid sample, the biosensor system being an optical system or an electrochemical system, the biosensor system comprising:
a test sensor having a base and a sample interface, the base forming a reservoir and a channel with an opening, the opening being configured to receive the biological fluid sample and to allow the biological fluid sample to flow through the channel to fill at least in part the reservoir, the reservoir being in electrical or optical communication with the measurement device, the test sensor having a chemical reagent reacting in a chemical reaction with the analyte in the biological fluid sample when the biological fluid sample is received in the reservoir;
a measurement device in electrical or optical communication with the reservoir, the measurement device having electrical circuitry communicatively coupled to a processor, a storage medium, a signal generator, and a sensor interface, the processor having instructions and data stored in the storage medium, the instructions configured such that when executed by the processor the system is enabled so that:
in response to the chemical reaction in the reservoir, the signal generator applies an electrical or optical input signal to the sensor interface, the input signal including at least one excitation having a time period with an end-point,
the input signal is transmitted by the sensor interface to the sample interface for applying the input signal to the biological fluid sample,
in response to the input signal and to the concentration of the analyte in the biological fluid sample, the processor generates one or more output signals from the test sensor during an excitation period,
the processor segments the one or more output signals during the excitation period of the one or more output signals into at least two segments with a regular or irregular segmenting interval, each segment including point readings obtained before the end-point of the input signal during the excitation period;
the processor converts the one or more output signals of the at least two segments into at least two signal processing parameters, wherein the segmented signal processing parameters describe a portion of a total error in the one or more output signals;
the processor determines a segmented signal processing function from the signal processing parameters;
the processor uses a predetermined reference correlation to relate the one or more output signals to a plurality of known sample analyte concentrations;
in response to the predetermined reference correlation, the processor uses a conversion function to convert the one or more output signals into one known sample analyte concentration of the plurality of known sample analyte concentrations;
the processor determines a compensated value from the one or more output signals in response to the conversion function and the segmented signal processing function;
the processor determines the analyte concentration in the biological fluid sample from the compensated value of the one or more output signals; and
the processor outputs the analyte concentration to one or more of a display, a remote receiver, or a storage medium.

20. The biosensor system of claim 19,
wherein the processor compensates at least 50% of the total error in the one or more output signals with a primary function, the primary function describing a major error in the one or more output signals and relating uncompensated output values and error contributors, the major error being attributable to one or more major error contributors selected from a group consisting of temperature, hematocrit, and hemoglobin; and
if the primary function is not the predetermined segmented signal processing function, the processor compensates at least 5% of the remaining error in the one or more output signals with the predetermined segmented signal processing function.

21. A method of operating a biosensor system for determining an analyte concentration in a biological fluid sample, the biosensor system being an optical sensor system or an electrochemical sensor system, the biosensor system including a measurement device and a test sensor, the measurement device having a processor, the test sensor being in electrical or optical communication with a reservoir, the method using the processor in performing steps comprising:

receiving the biological fluid sample in the reservoir of the test sensor, the biological fluid sample including the analyte;

applying an input signal to the biological fluid sample, the input signal including an excitation;

generating during an excitation period, via the biosensor system, an output signal responsive to the input signal and further responsive to the concentration of the analyte, the output signal being one or more of a light-generated output signal in response to a light-identifiable species and an electrical output signal generated by a redox reaction;

segmenting the output signal during the excitation period of the excitation into at least two segments, each segment including point readings obtained before an end-point of the excitation period;

converting the at least two segments into at least two signal processing parameters, the signal processing parameters describing a portion of a total error in the output signal;

determining a segmented signal processing function from the signal processing parameters;

determining a compensated value from the output signal in response to the segmented signal processing function;

determining the analyte concentration from the compensated value of the output signal; and outputting the analyte concentration to one or more of a display, a remote receiver, or a storage medium.

* * * * *